(12) United States Patent
Angelsen et al.

(10) Patent No.: US 6,485,423 B2
(45) Date of Patent: Nov. 26, 2002

(54) CORRECTION OF PHASEFRONT ABERRATIONS AND PULSE REVERBERATIONS IN MEDICAL ULTRASOUND IMAGING

(76) Inventors: Bjorn A. J. Angelsen, Bugges veg 4B, N-7051 Trodheim (NO); Tonni F. Johansen, Osloveien 6, N-7018 Trondheim (NO)

(*) Notice: Subject to any disclaimer, the term of this patent is extended or adjusted under 35 U.S.C. 154(b) by 56 days.

(21) Appl. No.: 09/773,335

(22) Filed: Jan. 31, 2001

(65) Prior Publication Data

US 2002/0002333 A1 Jan. 3, 2002

Related U.S. Application Data

(60) Provisional application No. 60/179,196, filed on Jan. 31, 2000.

(51) Int. Cl.$^7$ .................................................. A61B 8/14
(52) U.S. Cl. ..................... 600/458; 600/443; 73/602; 73/627
(58) Field of Search ................................. 600/458, 443; 73/627, 602; 367/87

(56) References Cited

U.S. PATENT DOCUMENTS

| | | | | |
|---|---|---|---|---|
| 4,470,303 A | * | 9/1984 | O'Donnell | 73/602 |
| 6,023,977 A | * | 2/2000 | Langdon et al. | 367/87 |
| 6,131,458 A | * | 10/2000 | Langdon et al. | 600/443 |

* cited by examiner

Primary Examiner—Marvin M. Lateef
Assistant Examiner—Ruby Jain
(74) Attorney, Agent, or Firm—Cohen, Pontani, Lieberman & Pavane

(57) ABSTRACT

A method of correcting for phasefront aberrations in ultrasound imaging uses highly spaced apart point scatterers artificially placed in the tissue being imaged. The point scatterers reflect the transmitted sound and are individually differentiated to provide singular reference points for correction of signals reflected from the surrounding tissue. The differentiation is performed by comparison of the third or fourth harmonic frequencies of the reflected signals. To ensure the necessary high dispersal of the point scatterers, high amplitude pulses of the transmitted signal destroy point scatterers in selected image regions. In an alternate embodiment, correction is performed by stochastic analysis of signals reflected from the highly dispersed point scatterers. A reference signal is compared to the second harmonic of the reflected signal to reduce noise.

43 Claims, 11 Drawing Sheets

CORRECTION OF PHASEFRONT ABERRATIONS AND PULSE REVERBERATIONS IN MEDICAL ULTRASOUND IMAGING

This application claims priority from Provisional application Ser. No. 60/179,196, filed Jan. 31, 2000.

BACKGROUND OF THE INVENTION

1. Field of the Invention

The present invention is directed to methods for estimating corrections for the image degradation produced in medical ultrasound images by phasefront aberrations and reverberations. The method hence has applications to all situations were ultrasound imaging is used in medicine, and also other similar situations of ultrasound imaging.

2. Description of the Related Art

With ultrasound imaging of objects through complex structures of tissue, the following effects will degrade the images i) Variations of the acoustic velocity within the complex tissue structures produce aberrations of the acoustic wavefront, destroying the focusing of the beam mainlobe and increasing the beam sidelobes.* ii) Interfaces between materials with large differences in acoustic properties can give so strong reflections of the ultrasound pulse that multiple reflections get large amplitudes. Such multiple reflections are termed pulse reverberations, and add a tail to the propagating ultrasound pulse, which shows as noise in the ultrasound image.*

The reduced focusing of the beam main lobe reduces the spatial resolution in the ultrasound imaging system. The increase in beam side lobes and the pulse reverberations, introduce additive noise in the image, which is termed acoustic noise as it is produced by the transmitted ultrasound pulse itself. Increasing the transmitted pulse power will hence not improve the power ratio of the signal to the noise of this type, contrary to what is found with electronic receiver noise.

The materials with largest differences in acoustic properties are muscles, fat, connective tissue, cartilage, bone, air, and the ultrasound transducer itself. Mixtures of fat, muscles, connective tissue and cartilage in the body wall can therefore produce very large phase front aberrations and reverberations. Especially, one will get strong reverberations from the transducer reflections of the returning signals from interfaces of such tissues in the body wall. The mixtures of such tissues in the body wall are therefore the major cause of the degradation found with non-invasive ultrasound imaging in many patients. Reducing the effect of the reverberations and phase front aberrations in the body wall is hence much needed in many applications of medical ultrasound imaging.

With a two-dimensional transducer array, the effect of the phasefront aberrations can in many situations be reduced by adding corrective delays and gain factors to the signals for the individual array elements, in the following referred to as element signals. This has been presented in many papers. In more complex situations of tissue mixtures, the phasefront aberrations and pulse reverberations can produce modifications of the pulse form. It is less known that such pulse modifications can be corrected by a filter for each of the element signals. Such correction filters gives the most general correction method, and delay/amplitude corrections can be considered as a special case or an approximation of correction filters.

$2^{nd}$ harmonic ultrasound imaging reduces the body-wall reverberations and the phasefront aberrations. The basis for this method is that the wave propagation velocity increases with the pressure amplitude, so that the positive pressure swing gets a higher propagation velocity than the negative pressure swing. This produces a non-linear propagation distortion of the forward propagating pulse that increases with the transmitted pulse amplitude. The distortion first increases with the propagation depth, producing higher harmonic frequency bands in the pulse oscillation. However, because of the power absorption of ultrasound in tissue increases with frequency, the distortion reaches a maximum and finally reduces for large depths.

Transmitting a pulse with center frequency around $f_0 \approx 1.5$ MHz, one gets adequate power in the $2^{nd}$ harmonic band around $2f_0 \approx 3$ MHz for imaging of the heart and other organs in the 3–15 cm range. The power in the higher than the $2^{nd}$ harmonic component is so low that it is not useful for imaging.

The $2^{nd}$ harmonic imaging has two advantages above first harmonic imaging around the same receive frequency:

i) The $2^{nd}$ harmonic amplitude is very low as the outbound pulse passes the body wall, so that the $2^{nd}$ harmonic components in the body-wall reverberations are low.* ii) As the transmitted frequency $f_0$ is low, the first harmonic transmitted beam is less affected by phase aberrations in the body wall. The $2^{nd}$ harmonic beam is also generated over a certain volume, which makes the $2^{nd}$ harmonic beam less sensitive to phase aberrations, and the field past the focus is also more collimated than for a $1^{st}$ harmonic beam at $2f_0$.* These two effects hence produce less body-wall reverberations and phase aberrations in the $2^{nd}$ harmonic pulse compared to the $1^{st}$ harmonic pulse at the same frequency.

However, when the back-scattered signal passes the body wall on its return, the $2^{nd}$ harmonic components are subject to the same amount of phasefront aberrations and pulse reverberations as the $1^{st}$ harmonic pulse. Corrections for phasefront aberrations and pulse reverberations in the receive beamformer, hence improves the receiver resolution and acoustic noise, in the same way as for the $1^{st}$ harmonic image. Also, there will be some residual phasefront aberrations and body-wall reverberations in the transmitted $2^{nd}$ harmonic pulse, which can further be reduced by corrections in the transmit beam former.

SUMMARY OF THE INVENTION

Although the principle of correction for phasefront aberrations and pulse reverberations is well defined, it is in the imaging situation generally difficult to determine the correction filters or the simplified delay and amplitude corrections. The present invention devices two solutions to this problem:

i) The backscattered signal from point scatterers that are artificially introduced into the body serves as beacons to determine the correction filters. Such point scatterers are either connected to intervention tools that are introduced into the body, for example a biopsy needle, or ultrasound contrast agent bubbles in such a dilute concentration that the signals from individual bubbles can be discriminated from each other. The point scatterers must be so spaced apart that the signals from different point scatterers are clearly differentiable from each other and be so strong that they are differentiable from the tissue signal. To maintain adequate distance between the bubbles, the invention devices to use high transmitted pulse amplitudes to destroy the bubbles in selected image regions, so that for an adequate interval of time after this bubble destruction, new inflow bubbles have adequate distance to each other. Consecutive transmission of high amplitude pulses into the region can be used for repeated destruction of the bubbles so that a continuously changing set of point scatterer bubbles in the image region is obtained. To discriminate the bubble signal from tissue signal one can typically use backscattered frequency components in a band around the the $3^{rd}$ or $4^{th}$ harmonic component of the transmit frequency band, or sub-harmonic components. Transmission of coded sequences with pulse compression of the received signal can also be used to improve the signal to noise ratio in the received signal from the contrast agent bubbles, and hence the detection of the signal. Spaced apart contrast agent bubbles can also be used as point scatterers on the intervention tool.* ii) With the other method one uses stochastic analysis of the back-scattered signal from distributed scatterers with short correlation length compared to the wave length. One general problem for such analysis is that the backscattered signal is corroborated with acoustic noise from pulse reverberations and phase front aberrations, and the invention devices two methods for reduction of such acoustic noise before the determination of the correction filters:

a) The $2^{nd}$ harmonic component of the backscattered element signals, which has reduced acoustic noise, is used for the analysis. However, this requires one filter per element signal, and the invention therefore also devices a simplified method of using the $2^{nd}$ harmonic component of the backscattered signal, where filtering of the individual element signals is avoided. In this method, the element signals are compared with a reference signal obtained from the element signals, the reference signal being modified so that the 1st harmonic band in the reference signal is highly attenuated, for example through filtering or pulse inversion techniques that are commonly known.* b) The body wall pulse reverberations are fairly stationary in time. By using the backscattered signal from moving or time varying scatterers obtained with multiple transmit pulses with the same focus and beam direction, the temporally stationary acoustic noise is suppressed by highpass filtering each range in the backscattered signal along the pulse number coordinate, so that mainly the signals from the moving scatterers passes the filter for further processing. Typical moving scatterers can be the myocardium or an arterial wall, or scatterers found in blood or other body fluids. To enhance the scattering from such fluids, the invention also devices the use of ultrasound contrast agent to be injected into the body fluid. Time varying scatterers can be ultrasound contrast agent where so high transmit pulses are used that one get destruction of at least some of the contrast agent bubbles between the pulses.*

The stochastic analysis commonly contains an averaging of signal parameters, where averaging of signal parameters from different depths or possibly also different beam directions typically can be used. Such methods often provides a limited number of samples to average, which gives variance noise in the estimates.

To improve the estimation robustness and reduce the variance in the estimates, the invention devices a method that uses the backscattered signal from moving or time varying scatterers acquired with multiple transmit pulses with the same focus and beam direction. Signal parameters obtained for each transmit pulse are then averaged for many transmit pulses, possibly in combination with averaging over depth and beam direction, to reduce the variance in the estimates.

In addition to these basic principles, the invention devices several detailed methods for estimation of the correction filters.

Strong scatterers off the beam axis, can introduce interference in the correction estimates, and the invention devices methods to reduce the effect of such scatterers, using spatial lowpass filtering of the received signal across the transducer surface, or highpass filtering of estimated correction phases or delays across the transducer surface. Such highpass filtering can conveniently be done by expanding the correction delays in a generalized Fourier series, for example using Legendre polynomials as basis functions, and leaving out the lowest coefficients that relates to offset direction and possible offset focusing of the scatterer.

The correlation length of the phase aberrations and pulse reverberations along the transducer array surface has a lower bound. One can therefore also truncate the generalized Fourier series at the upper end, reducing the total number of coefficients in the series. The information carrying coefficients in the generalized Fourier series is hence a reduced parameter set that represents the correction filters, and is conveniently estimated in a parameter estimation scheme.

Often one also find that the correlation length of the phase aberrations and pulse reverberations along the transducer array surface is larger than the array element dimensions, as for example with phased arrays for sector steering of the beam. For this situation the invention devices combination of the element signals from neighboring elements before estimation of the correction filters. This combination reduces the total number of signal channels used in the estimation, hence simplifying the processing and increasing the signal to noise ratio in the resulting channel.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1:
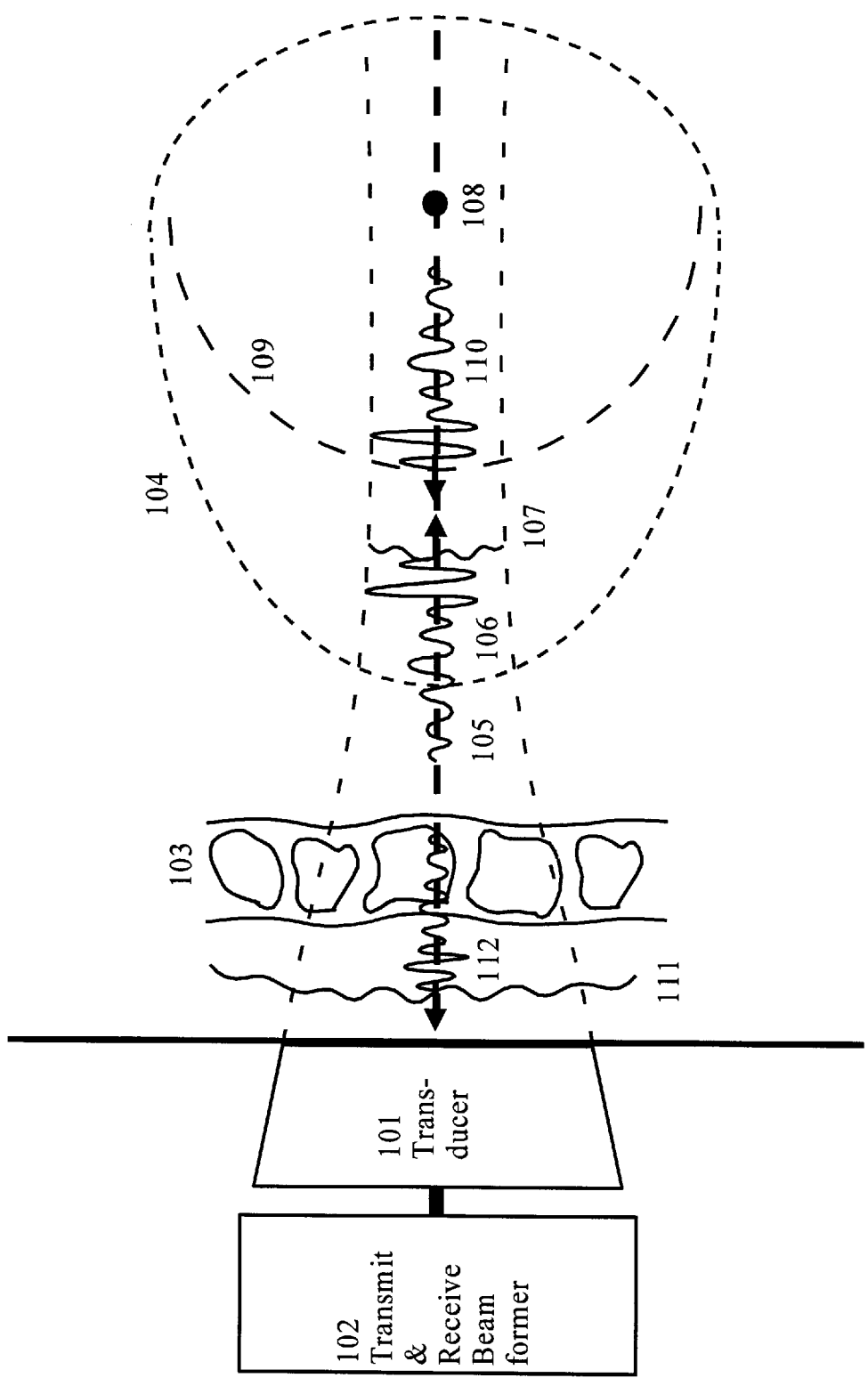
FIG. 1 shows a typical measurement situation where the ultrasound array in contact with the skin transmits ultrasound pulses through the body wall, which is a mixture of fat, muscles, and connective tissue. The outbound pulse is modified by phase aberrations and pulse reverberations as it passes the body wall. A point scatterer, scatters a spherical wave which is modified by reverberations and phase front aberrations as it returns through the body wall.

FIG. 1 shows a typical measurement situation where an ultrasound transducer array (101) driven by a transmit beam former (102), transmits a pulsed and focused ultrasound beam through the body wall (103) towards an object (104) to be imaged. The body wall is a heterogeneous mixture of fat, muscles, and connective tissue with differences in acoustic velocity and characteristic impedance. Multiple reflections within the body wall and between structures in the body wall and the transducer, produces a reverberation tail (105) to the transmitted pulse (106) as it passes the wall. Similarly, the variations in the acoustic velocity produce aberrations of the phasefront (107) as the pulse passes the wall.

At reflection of the pulse from a point scatterer (108) within the object, a wave with spherical wave front (109) is reflected, while the temporal variation of the pulse with reverberation tail is preserved (110). In passing the body wall on its path back to the transducer array, aberrations of the pulse phasefront (111) occur, and additional reverberations of the pulse is found (112).

Figure 2:
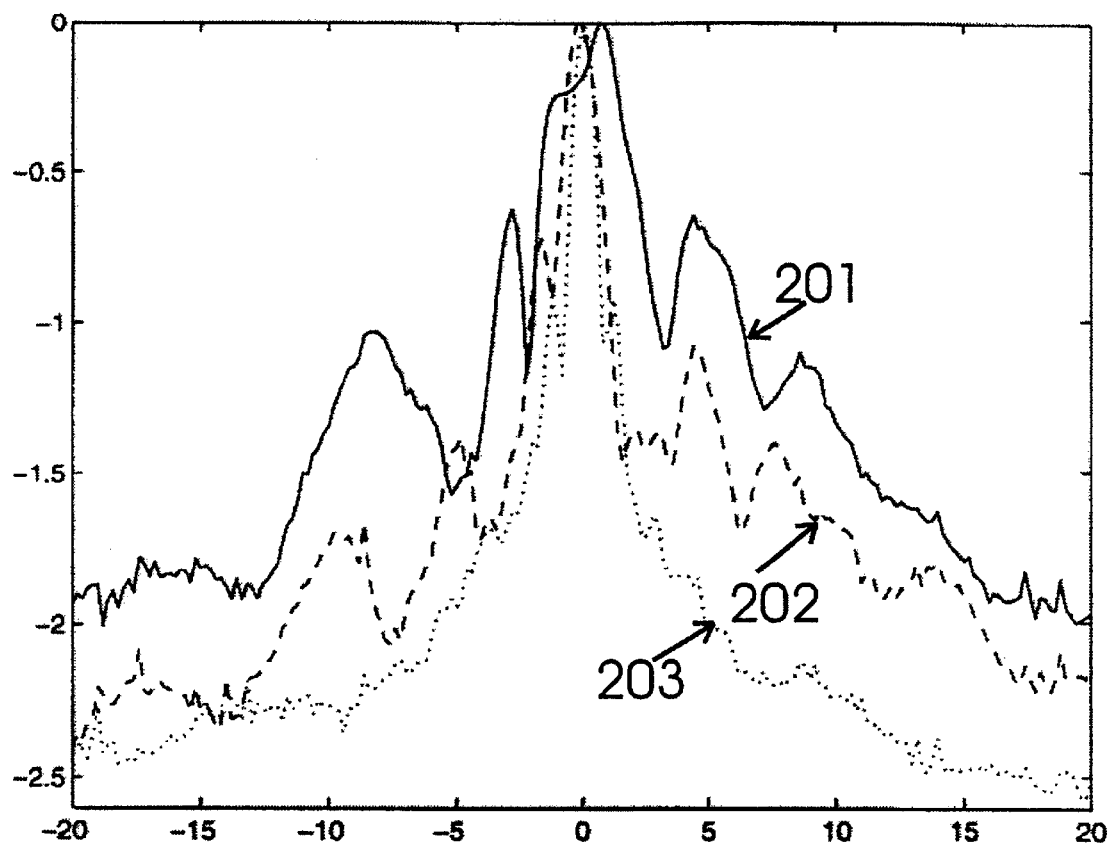
FIG. 2 shows an example of a practical focal plane beam profile that is obtained for a phase aberrated pulse together with a corrected beam profile and the ideal beamprofile obtained without phase aberrations.

In order to focus the receiver beam onto the point scatterer, a standard receiver beam former will delay the individual array signals a time interval calculated from the assumption that the wavefront that arrives from the point scatterer has a spherical shape. Amplitude apodization of the array element signals is also used to reduce the sidelobes in the focal plane. When the real phase front (111) is not ideally spherical due to aberrations, the standard beam former produces a less than ideal focus of the receiver beam. This is illustrated by the focal beam profile 201 of FIG. 2. Using corrective delays on the element signals, one is able to produce an improved focal beam profile as 202 in the Figure. For comparison, the Figure also shows the focal beam profile 203 that is obtained for wave propagation in water.

In the linear approximation of wave propagation in the tissue, all aspects of the propagation is contained in the Green's function. This function gives the wave-field from a unit point source located at all source points $\underline{r}_f$ in space. In the temporal frequency domain, we describe the Green's function as $g(\underline{r},\underline{r}_f;\omega)$, and it gives the field at the field-point $\underline{r}$ from a unit point source located at the source-point $\underline{r}_f$ and radiating continuous, time harmonic waves with temporal angular frequency $\omega$. In the following analysis we relate the Green's function for heterogeneous tissue mixtures to the free-space Green's function $g_h(\underline{r}-\underline{r}_f;\omega)$ for a homogeneous material as $$g(\underline{r},\underline{r}_f;\omega)=s(\underline{r},\underline{r}_f;\omega)g_h(\underline{r}-\underline{r}_f;\omega) \tag{1}$$

where $$g_h(\underline{r}-\underline{r}_f;\omega) = \frac{e^{-ik|\underline{r}-\underline{r}_f|}}{4\pi|\underline{r}-\underline{r}_f|} \quad k=\omega/c \tag{2}$$

c is the wave propagation velocity in the homogeneous tissue. $s(\underline{r},\underline{r}_f;\omega)$ is called the frequency dependent phase-amplitude screen for a scatterer at location $\underline{r}_f$. We hence see that $s(\underline{r},\underline{r}_f;\omega)$ represents both the phase aberration and reverberation distortion of the body wall on the wave propagation.

When there is no power absorption in the tissue, it has been shown by M. Fink [1], that time-reversal of the received element signals from a point source in a two-dimensional array, produces the optimal correction of the element transmit signals, for focusing the transmit beam onto the point source. This is equivalent to setting up the transmit beam former in the standard way assuming homogeneous tissue with constant wave velocity, and then filtering the transmit pulses at the element location $\underline{r}$ on the transducer surface, with the time reversal filter $$H_{tr}(\underline{r},\underline{r}_f;\omega)=s^*(\underline{r},\underline{r}_f;\omega) \tag{3}$$

where * denotes complex conjugation. By reciprocity of the transmit and the receive beams, we also get optimal focusing of the receive beam onto the point target at $\underline{r}_f$, by filtering the element receive signals at location $\underline{r}$ with $H_{tr}(\underline{r},\underline{r}_f;\omega)$.

The reason one must use a two-dimensional array for corrections of the body wall disturbances is that the body wall produces a two-dimensional disturbance pattern over the transducer array. The correlation length of the disturbances has however a lower limit, so that the width of the elements used in the correction can be larger than typical element widths in many electronic arrays, for example the phased array. For efficient processing, one can in such situations combine the element signals from neighboring, narrow elements to give fewer element signals from larger elements, that are still smaller than the correlation length of the disturbances over the array.

With uniform acoustic power absorption in the tissue, the gain and phase variations of s* will still correct for the spatial variations in propagation velocity in the tissue and hence reduce the effect of phase aberrations and pulse reverberations. The absorption will, however, attenuate the pulse and also produce some pulse stretching since the power absorption increases with frequency. These effects can be compensated for by a depth variable gain and filter. Strongly heterogeneous absorption will produce spatial amplitude variations in the Green's function that requires special compensation not accounted for by $H_{tr}$ in Eq.(3).

From the definition in Eq.(1) we see that one can determine $s(\underline{r},\underline{r}_f;\omega)$ from the signal from a point scatterer located at $\underline{r}_f$, with a received signal that is clearly differentiable from that of the surrounding tissue. However, it is rare to find such point scatterers in the tissue, and it is hence a challenge to determine $s(\underline{r},\underline{r}_f;\omega)$.

In a first aspect, the invention devices the introduction of artificial point scatterers with signal that is clearly differentiable in amplitude or frequency content from the tissue signal, so that $g(\underline{r},\underline{r}_{fk};\omega)=s(\underline{r},\underline{r}_{fk};\omega)g_h(\underline{r}-\underline{r}_{fk};\omega)$ can be determined, where $\underline{r}_{fk}$ are the positions of the point scatterers that are used for corrected focusing of the transmit and receive beams onto all $\underline{r}_{fk}$'s according to Eq.(3). One then can calculate $s(\underline{r},\underline{r}_{fk};\omega)=g(\underline{r},\underline{r}_{fk};\omega)=g_h(\underline{r}-\underline{r}_{fk};\omega)$. The distance between the point scatterers then must be so large that the signals from the point scatterers also are differentiable from each other.

Figure 3A:
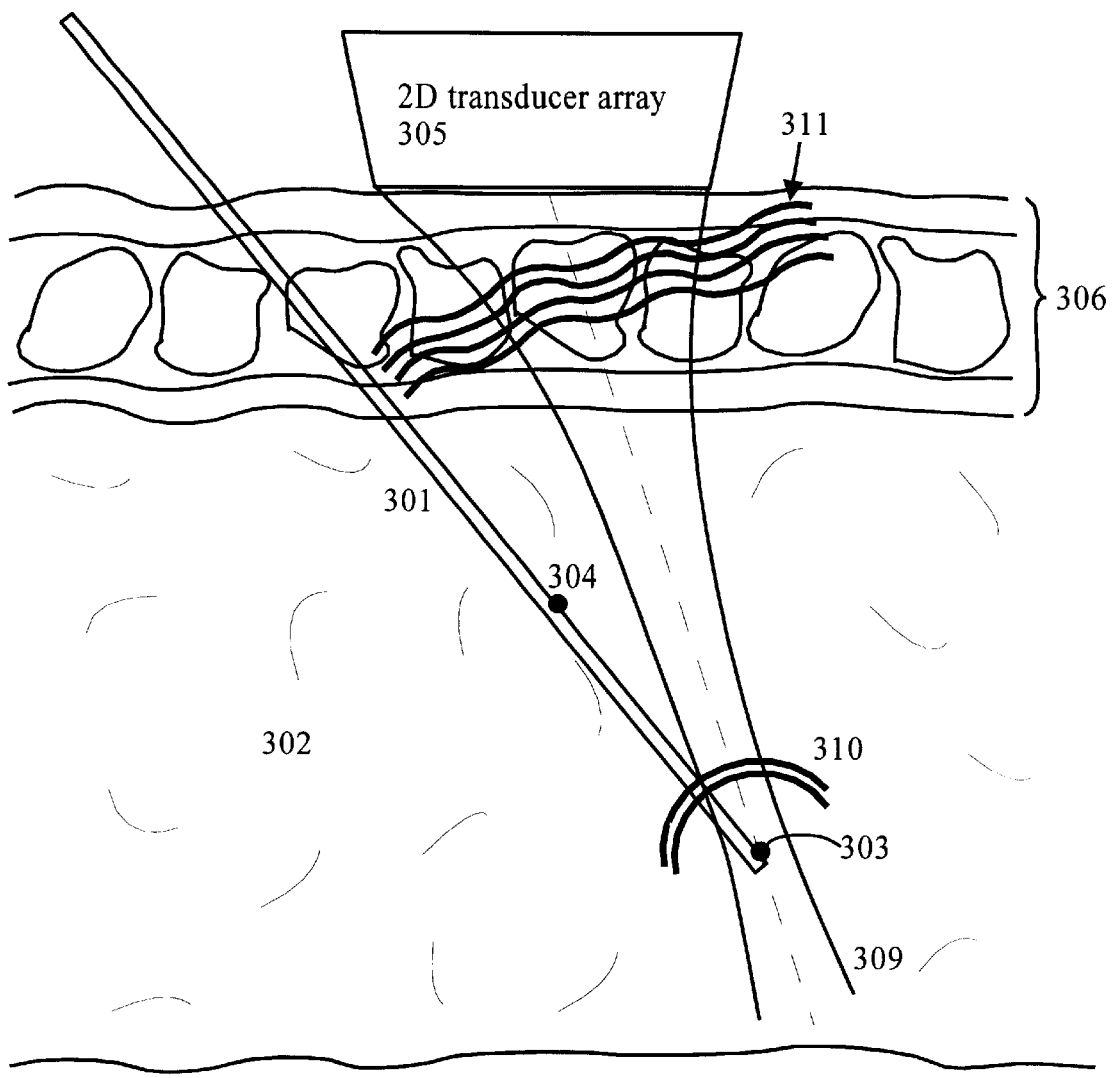
FIG. 3 In a) shows the use of artificially introduced point scatterers on an intervention tool for estimation of correction filters. In b) is shown an example block diagram of a unit for estimation of correction filters both from point scatterers and distributed scatterers, and how the correction filters are used for corrections of phase aberrations and pulse reverberations both in the receiver and the transmit beams.
Figure 3B:
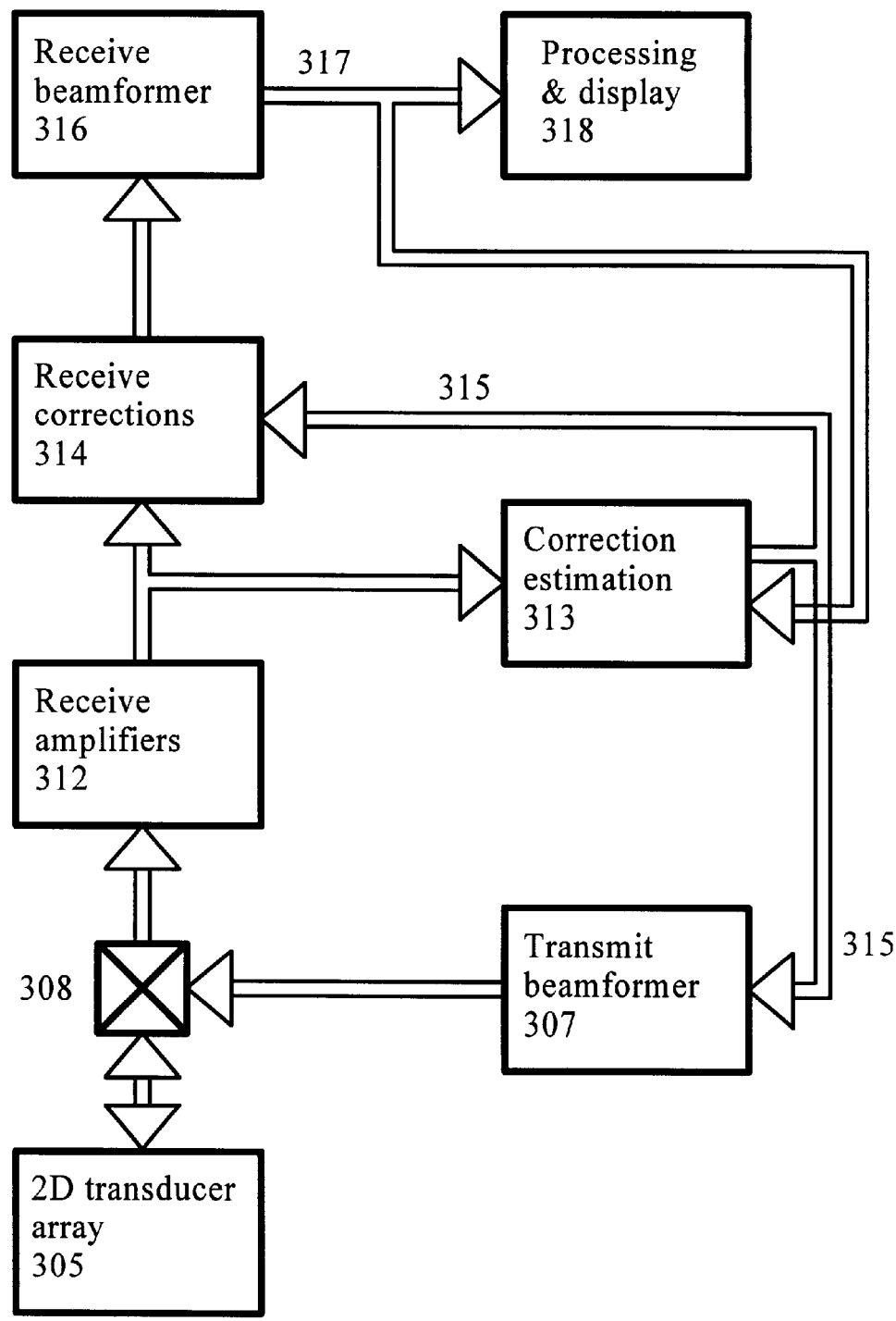

According to the invention, the point scatterers can be introduced on an intervention tool, like a biopsy needle, for improved imaging of the tissue around the needle, especially the biopsy target around the needle tip and also to avoid critical areas around the needle tip when it is introduced, like blood vessels. An example of such a situation is shown in FIGS. 3a and 3b, where 301 shows the intervention tool imbedded in the tissue 302, with two point scatterers 303 and 304 attached to the tool. The point scatterers could also be made as a ring or point indentation in the tool. A two-dimensional transducer array 305 at the surface of the body wall 306 is driven by a transmit beam former 307 shown in FIG. 3b, that is connected to the array via a transmit/receiver switch 308 to emit focused, pulsed ultrasound beams that are direction scanned into the tissue. In this particular depiction the array is shown to transmit a beam 309 that is directed against the point scatterer 303, which backscatters a spherical wave 310. When this spherical wave passes the body wall, it is modified due to phase front aberrations and pulse reverberations as exemplified by 311, before it is picked up by the array 305, that shortly after the pulse transmission is connected via the switch 308 to receiver amplifiers 312 and a correction estimation unit 313, in parrallel to a receive correction unit 314, followed by a receiver beamformer 316 that feeds the output to an ultrasound image processing and display unit 318.

The correction estimation unit 313 estimates $s(\underline{r},\underline{r}_f;\omega)$ where $\underline{r}_f$ in this particular example is the location of point scatterer 303. The correction filter transfer functions according to Eq.(3) are transferred via 315 to the receive correction unit 314, where the receive element signals are correction filtered and possibly combined to fewer element signals as described below, before they are transmitted to the receiver beam former 316. This beam former can be of a standard type and has as its output standard ultrasound receive RF-lines 317, possibly for a multitude of neighboring parallel receive directions. The received RF-lines are fed to an ultrasound image processing and display unit 318, that generates and displays full ultrasound tissue and velocity images, as well as ultrasound Doppler spectra, according to known principles.

The received ultrasound RF-lines 317 could also conveniently be transferred to the correction estimation unit 313 to be used in some estimation algorithms like the reference signal correlation method described in Eqs.(68–74, 90–94) below. Such reference signals could also conveniently be generated within the correction estimation unit itself.

As the first point scatterer 303 is located near the tip of the tool 301, one will get a corrected image around the tool tip as it is introduced into the tissue. When the beam direction scans, the correction estimation unit 313 will also detect the other point scatterers and produce corrected images in a region around these point scatterers also.

Figure 4A:
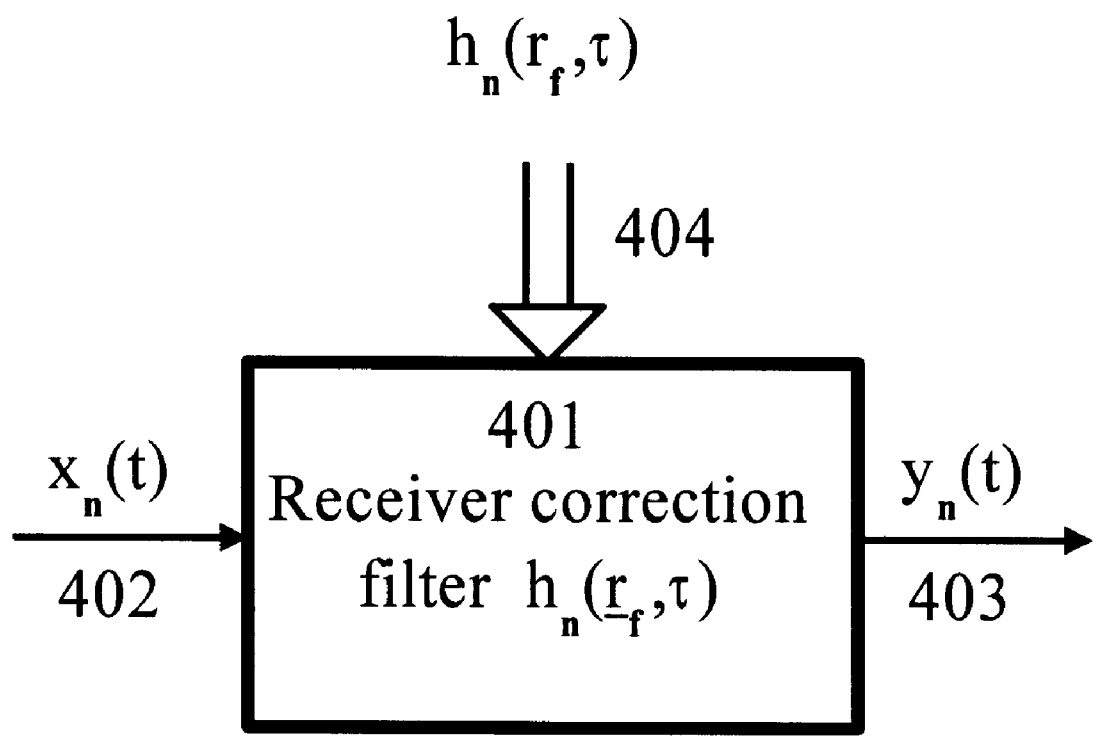
FIG. 4 shows in a) a block diagram of a FIR filter for corrections of element signal no. n in the receiver beam former, while in b) is shown a unit for correction of transmitted signal on element no. n in the transmit beam former.

Corrections of the receive element signals could typically be done in a filter unit shown for one single element signal no n as 401 in FIG. 4a. The frequency response of this filter is for focusing onto $\underline{r}_f$ given as $H_n(\underline{r}_f;\omega)=H_n(\underline{r}_n,\underline{r}_f;\omega)$ according to Eq.(3), and the impulse response $h_n(\underline{r}_f;\tau)$ is the inverse Fourier transform of $H_n(\underline{r}_f;\omega)$. This unit takes as input an unmodified signal $x_n(t)$ from element no n, shown as 402 in the Figure, and produce the corrected signal $y_n(t)$ (403) for further processing in the receive beam former. The simplest form of the correction filter is a pure delay function and possible amplitude modification according to the discussion below, in particular in relation to Eqs.(78–94). The receive correction unit could also conveniently combine several channels with minimal nominal delays, for example focusing without direction steering in the elevation direction of the array (y-direction in FIG. 6). The element signals in the elevation direction (y-direction) can then be added in the correction unit for each azimuth position (x-direction of FIG. 6) to reduce the required number of channels in the receiver beamformer 316.

Figure 4B:
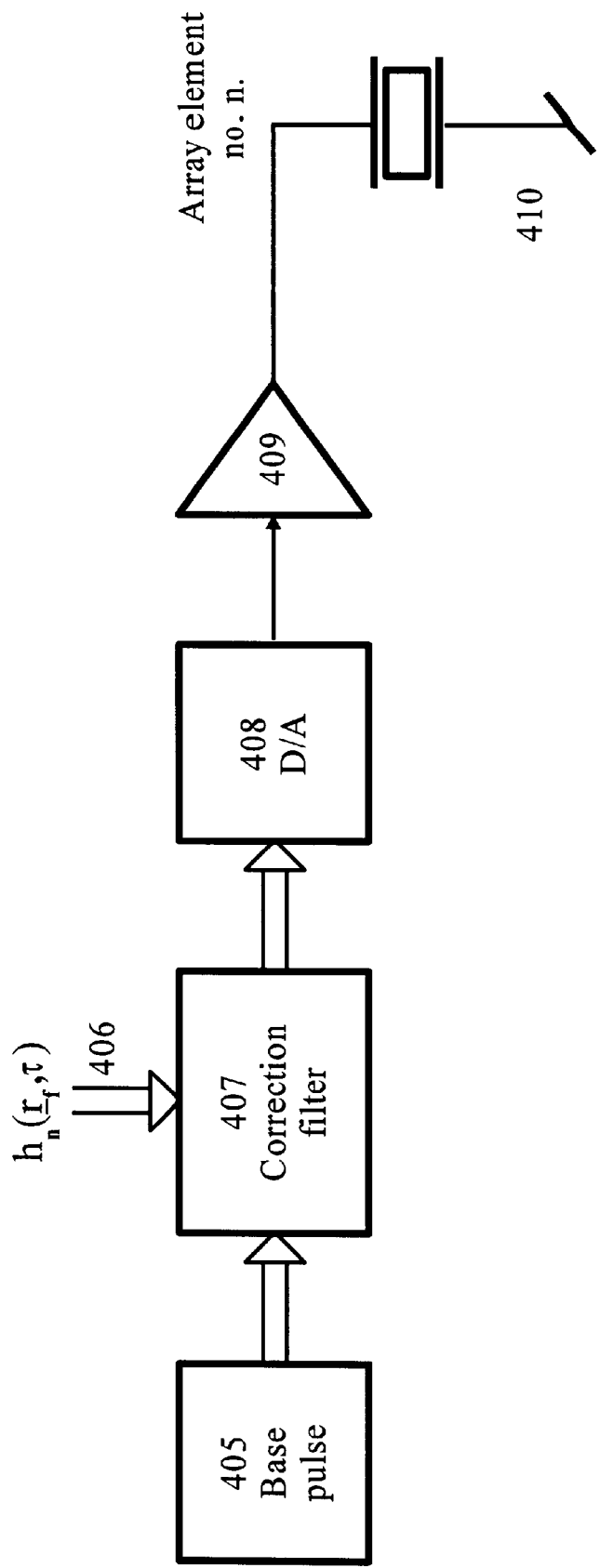

The output 315 of the correction estimation unit could also conveniently be transferred to the transmit beamformer 307 to modify the transmit pulses to obtain a phase aberration and reverberation corrected beam. The simplest correction is then a delay of the transmit pulse and possibly an amplitude modification. Complex correction according to the full filter in Eq.(3) can for example be obtained for each channel by the unit in FIG. 4b, where the digital representation of the base pulse is stored in a unit 405, and the correction filter impulse response as the inverse Fourier transform of Eq.(3) is set as the coefficients 406 of a transversal filter unit 407. The output of this filter unit is fed to a D/A converter 408 and and the transducer drive amplifier 409 that drives the transducer element no n, 410, possibly via a cable.

Figure 5:
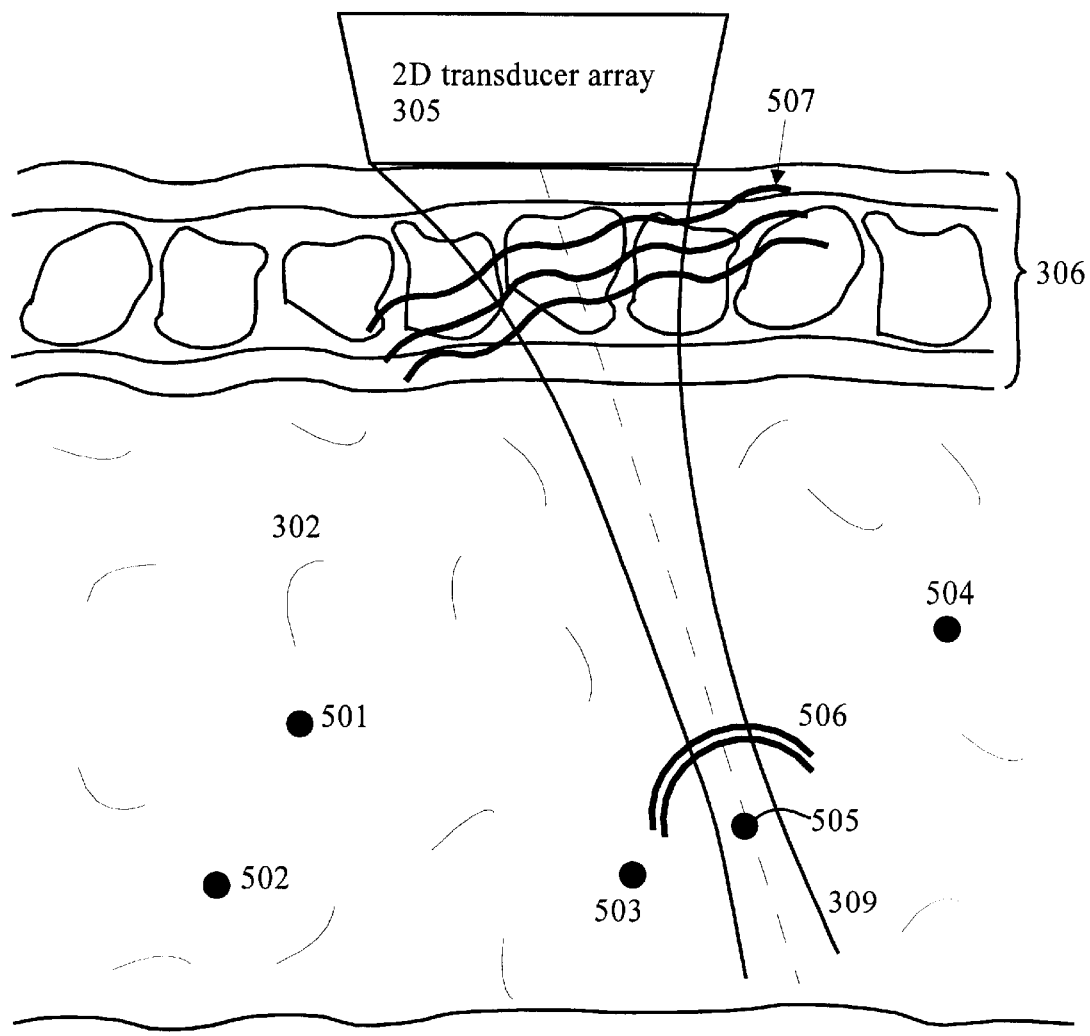
FIG. 5 shows the use of artificially introduced point scatterers in the form of contrast agent bubbles that are introduced at low concentration in the blood or other body fluids.

According to the invention, the point scatterers can also be introduced as a dilute concentration of contrast agent bubbles, so that the bubbles in the tissue are so spaced apart that their signals can be discriminated from each other, as illustrated in FIG. 5. This Figure shows as in FIG. 3 the same 2D transducer array 305, body wall 306, tissue 302, and transmit beam 309, which are given the same numeration, where the intervention tool is removed and substituted with a set of contrast agent bubbles 501–505 for the sake of example. To obtain adequately spaced apart contrast bubbles, one can first destroy all contrast bubbles in selected image regions by transmitting high amplitude pressure pulses. The low concentration of contrast bubbles in the inflow arteries will then introduce new bubbles at random locations in the tissue so that in an adequate time interval after the destruction, the new bubbles have adequate distance to each other. With moderate transmit amplitudes one can obtain destruction of a fraction of the contrast agent bubbles for each pulse, which together with the continuous inflow through the tissue blood perfusion produces a time variable set of point scatterers.

Each contrast bubble reflects when they are hit by an incident ultrasound pulse, a set of non-linearly distorted pulses that propagates as spherical waves, where one in the example illustrates the wave 506 reflected from contrast bubble 505. When propagating through the body wall, the wave is distorted by phase aberrations and pulse reverberations, indicated as 507 in the Figure, similar to 311 in FIG. 3.

To discriminate contrast bubble signal from the surrounding tissue signal, one can use the sub, $2^{nd}$, $3^{rd}$ or $4^{th}$ harmonic component of the backscattered signal, that are weak for the tissue signal, but still strong for the contrast bubble signal. The correction filter estimator unit 313 then contains extra filter units that select the selected harmonic components of the back scattered signal in each element signal.

To avoid unwanted destruction of the contrast agent bubbles, the incident pulse amplitude in the tissue must be kept limited. Maintaining this limit in the incident pulse, one can improve the signal to noise ratio in the received element signals by transmission of coded pulse sequences with subsequent pulse compression in the receiver, and hence reduce the noise in the estimated $s(\underline{r},\underline{r}_f;\omega)$.

Such contrast bubbles are also good candidates for point scatterers to be attached at localized sites on intervention tools.

In the second aspect of the invention, the present patent devices a method for estimating $s(\underline{r},\underline{r}_f;\omega)$ from the backscattered signal from a distribution of scatterers that can be modeled by a stochastic ensemble with short correlation length so that δ-correlation of the scatterers is an adequate approximation. The acoustic noise in the signal is heavily attenuated before the estimation of s by using $2^{nd}$ harmonic processing or signal from moving or time varying scatterers. The signal from such scatterers can also be used to reduce variance and noise in the estimates. Ultrasound contrast agent can also be used in these materials to enhance the scattering from the materials. Destruction of the contrast agent by the incident pulses can also be used to generate time varying scatterers in a region. Specially designed algorithms can be used to estimate parametric representations of $s(\underline{r},\underline{r}_f;\omega)$.

A presupposition is that the scatterers used to estimate $s(\underline{r},\underline{r}_f;\omega)$ can be modeled as a δ-correlated ensemble of scatterers. This means that each outcome of the ensemble represents a spatial distribution of the scatterers $v(\underline{r})$ so that averaging over the ensemble we get the following δ-correlation of the scatterer distribution $$<v(\underline{r}_1)v(\underline{r}_2)>=\sigma_v^2(\underline{r}_1)\delta(\underline{r}_2-\underline{r}_1) \quad (4)$$

< > denotes ensemble averaging over a mathematically defined outcome ensemble to be further discussed below, and $\sigma_v^2(\underline{r}_1)$ is the variance parameter of the distribution at location $\underline{r}_1$. We should note that the δ-correlation is an approximation when the correlation length of the scatterer distribution is adequately short to do the approximations from Eq.(14) to Eqs.(15, 35, 70), etc.

The outcome ensemble is a selected set of scattering distribution functions, where the particular scatterer distribution found in an experiment is considered an outcome or realization of the ensemble. As one in the experimental situation can not observe all outcomes of the ensemble, it is with practical experiments generally a problem to carry through an ensemble averaging as defined above. For spatially stationary scatterer distributions, one can to a limited degree substitute ensemble averaging with spatial averaging over the regions of scatterer positions $\underline{r}_1$ where $s(\underline{r},\underline{r}_1;\omega)$ is practically independent of $\underline{r}_1$.

The present invention also devices an additional method for estimating ensemble averaging of signal parameters, where one uses the signal from moving scatterers observed with consecutive transmit pulses with the same focus and amplitude, separated with so large intervals in time that the scatterers are exchanged in the actual region for each transmit pulse. Hence, the signal from each transmit pulse can be considered as an outcome of the ensemble, and averaging of signal parameters for a particular region can be done by averaging over the signal from the consecutive transmit pulses, which is further described below.

To obtain time varying scatterers in a tissue region that otherwise has limited movement, and where adequately large blood vessels where the blood can be used as moving scatterers, are missing, one can insert ultrasound contrast agent into the blood vessels, which subsequently flows into the capillaries of the tissue region. With a high amplitude of the incident imaging pulses, some or all of the contrast agent bubbles within the beam can be destroyed. This destruction combined with the new inflow of contrast agent bubbles to the tissue region can be used to produce variation of the contrast agent bubbles in the imaging region between pulses. Temporal averaging of signal parameters of the backscattered signal from the contrast agent for a set of transmitted pulses, can then be used as an estimate of ensemble averages.

Using the expression for the Green's function in Eq.(1), we get the following expression for the spatial frequency response of the transmitted beam at $\underline{r}_1$, when the beam is focused at $\underline{r}_f$ $$H_t(\underline{r}_1,\underline{r}_f;\omega) = \int_{S_t} d^2r_0 \frac{e^{-ik|\underline{r}_1-\underline{r}_0|-i\omega\tau_{sf}(\underline{r}_0,\underline{r}_f)}}{2\pi|\underline{r}-\underline{r}_0|} s(\underline{r}_0,\underline{r}_1;\omega) \quad (5)$$

$$\omega\tau_{sf}(\underline{r}_0,\underline{r}_f) = kr_f - k|\underline{r}_0-\underline{r}_f|$$

where $S_t$ is the transducer surface. $\tau_{sf}(\underline{r}_0,\underline{r}_f)$ are the steering and focusing delays for an element $\underline{r}_0$ at to focus the beam at $\underline{r}_f$ in a homogeneous medium with wave propagation velocity of $c=\omega/k$.

Figure 6:
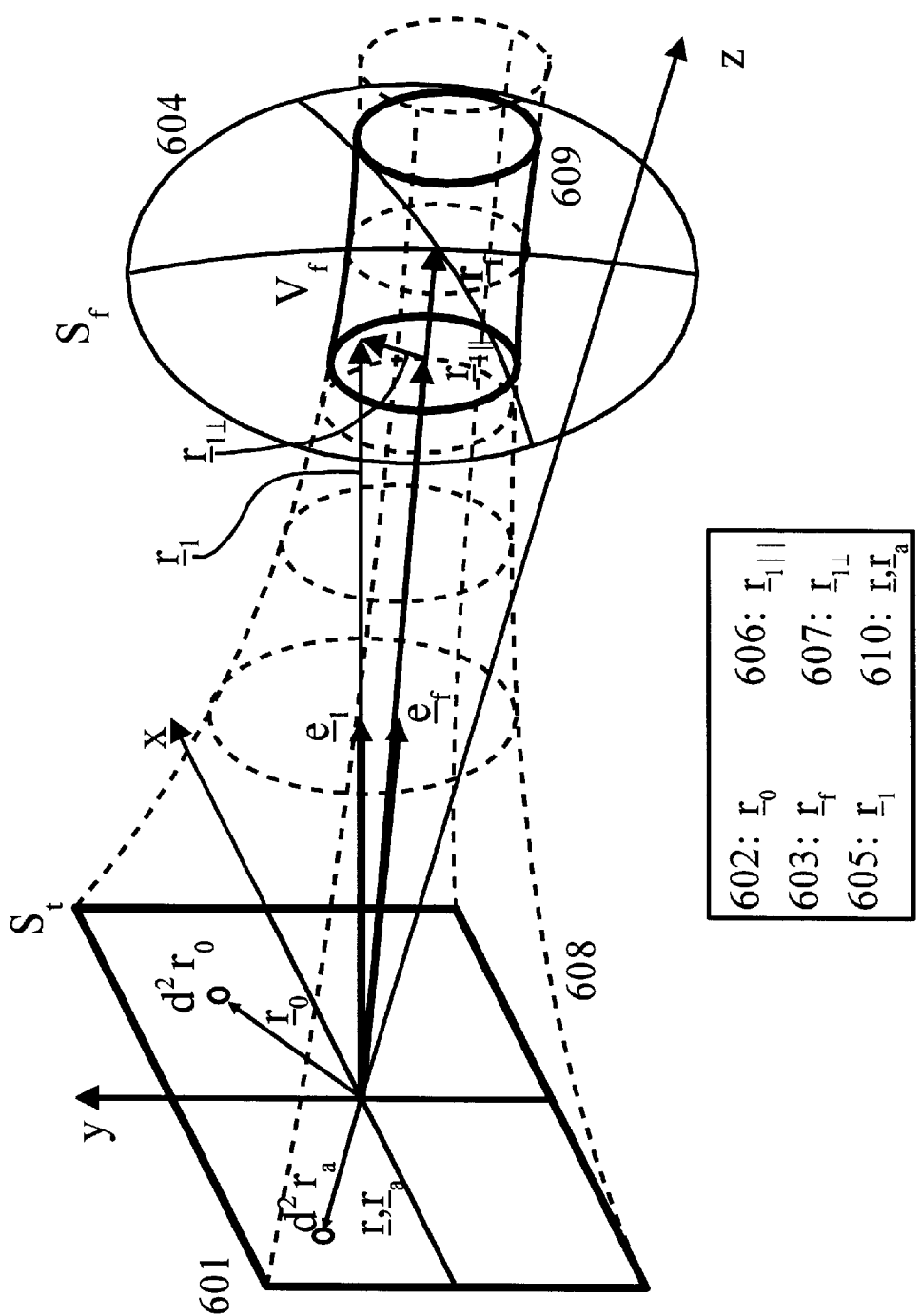
FIG. 6 shows the coordinate system used for calculating the expressions of the element signals.

The coordinates are illustrated in FIG. 6, where the transducer surface $S_t$ is shown as 601 with a source coordinate at the transducer $\underline{r}_0$ shown as 602. The vector coordinate $\underline{r}_f$ for the focus is shown as 603 with the focal surface $S_f$ shown as the spherical surface 604 with radius $r_f$ centered at the transducer center. The field-point determined by the field vector $\underline{r}_1$ is shown as 605. For the calculations below it is convenient to decompose $\underline{r}_1$ into a component $\underline{r}_{1\parallel}$ along $\underline{r}_f$ shown as 606, and a component $\underline{r}_{1\perp}$ orthogonal to $\underline{r}_f$ shown as 607, so that $\underline{r}_1=\underline{r}_{1\parallel}+\underline{r}_{1\perp}$. The focused beam is indicated as 608, where a selected region $V_f$ around the focus is shown as 609.

Around the focus $\underline{r}_f$, one can use the paraxial approximation of the exponent in Eq.(5) that gives $$-|\underline{r}_1-\underline{r}_0|-r_f+|\underline{r}_0-\underline{r}_f| \approx \quad (6)$$

$$-r_1+\underline{e}_1\cdot\underline{r}_0-\frac{r_0^2}{2r_1}-r_f+r_f-\underline{e}_f\cdot\underline{r}_0+\frac{r_0^2}{2r_f}=$$

$$-r_1+(\underline{e}_1-\underline{e}_f)\cdot\underline{r}_0+r_0^2(1/2r_f-1/2r_1)$$

where $\underline{e}_1=\underline{r}_1/r_1$ and $\underline{e}_f=\underline{r}_f/r_f$ are the unit vectors in the direction of $\underline{r}_1$ and $\underline{r}_f$, respectively. This expression allows us to approximate the transmitted field in Eq.(5) as $$H_t(\underline{r}_1,\underline{r}_f;\omega) = \frac{e^{-ikr_1}}{2\pi r_1}\int_{S_t} d^2r_0 e^{ik(\underline{e}_1-\underline{e}_f)\underline{r}_0+ikr_0^2(1/2r_f-1/2r_1)} s(\underline{r}_0,\underline{r}_1;\omega) \quad (7)$$

In the focal surface $S_f$ shown as 604 in FIG. 6, we have $r_1=r_f$, which gives $$H_t(\underline{r}_1,\underline{r}_f;\omega) = \frac{e^{-ikr_1}}{2\pi r_1} H_{et}(\underline{r}_1,\underline{r}_f;\omega) \quad (8)$$

-continued $$H_{et}(r_1, r_f; \omega) = \int_{S_t} d^2 r_0 \, e^{ik(\varepsilon_1 - \varepsilon_f)r_0} s(r_0, r_1; \omega)$$

The focal beam profile $H_{et}$ is hence the Fourier transform of the phase-amplitude screen. Close to the focal plane we see from the above that we can approximate $H_t$ as $$H_t(r_1, r_f; \omega) \approx e^{-ikr_1} F(r_1 - r_f) H_{et}(r_1, r_f; \omega) \qquad (9)$$

which will be used in the following analysis.

The temporal Fourier transform of the received signal at location $r$ on the receiving transducer array, shown as 610 in FIG. 6, from the region $V_f$ shown as 609 around the focus, is $$y(r; \omega) = P(\omega) \int_{V_f} d^3 r_1 2g(r, r_1; \omega) \sigma(r_1; \omega) \qquad (10)$$

$$= P(\omega) \int_{V_f} d^3 r_1 s(r, r_1; \omega) 2g_h(r - r_1; \omega) \sigma(r_1; \omega)$$

where $P(\omega)$ is the temporal Fourier transform of the received pulse from a point scatterer, and $\sigma(r_1; \omega)$ is a source density given as the product of the transmit beam and the scattering density as $$\sigma(r_1; \omega) = -k^2 H_t(r_1, r_f; \omega) \nu(r_1) \qquad (11)$$

We note from Eqs.(4, 11) that $\sigma$ is $\delta$-correlated in space, i.e.

$$\langle \sigma^*(r_1; \omega) \sigma(r_2; \omega) \rangle = \sigma_\sigma^2(r_1; \omega) \delta(r_2 - r_1) \quad \sigma_\sigma^2(r_1; \omega) = k^4 |H_t(r_1, r_f; \omega)|^2 \sigma_\nu^2 \qquad (12)$$

For steering and focusing the receive beam onto $r_f$, we correct y as $$y_f(r; \omega) = y(r; \omega) 2\pi r_f e^{-i\omega\tau_{sf}(r, r_f)} \quad \omega\tau_{sf}(r, r_f) = kr_f - k|r - r_f| \qquad (13)$$

where $\tau_{sf}(r, r_f)$ is the steering and focusing delays that focuses the receive beam onto $r_f$ for the homomgeneous medium, as in Eq.(5).

We shall now analyze a situation where the phase-amplitude screen varies so slowly with the scatterer position $r_1 \in V_f$ that we can approximate $s(r, r_1; \omega) \approx s(r, r_f; \omega)$, which allows us to take s outside the integral in Eq.(10). Eq.(13) can then be rewritten as a) $$y_f(r; \omega) = s(r, r_f; \omega) f(r, r_f; \omega) \qquad (14)$$

$$f(r, r_f; \omega) = P(\omega) \int_{V_f} d^3 r_1 \, g_f(r - r_1; \omega) \sigma(r_1; \omega)$$

b) $$g_f(r, r_1; \omega) = 4\pi r_f e^{-i\omega\tau_{sf}(r, r_f)} g_h(r - r_1; \omega)$$

$$= \frac{r_f e^{-ikr_f + ik|r - r_f| - ik|r - r_1|}}{|r - r_1|}$$

As $\sigma$ is a $\delta$-correlated process with zero mean, $y_f$ and $f$ will by the Central Limit Theorem be zero mean Gaussian processes. Hence, all information is contained in the $2^{nd}$ order moments, i.e. the auto-correlation function in space for $y_f(r, \omega)$ which is obtained from Eqs.(12, 14) as $$R_{yf}(r, \xi; \omega) = \langle y_f^*(r; \omega) y_f(r + \xi; \omega) \rangle \qquad (15)$$

$$= s^*(r, r_f; \omega) s(r + \xi, r_f; \omega) R_f(r, \xi; \omega)$$

-continued $$R_f(r, \xi; \omega) = |P(\omega)|^2 \int_{V_f} d^3 r_1 g_f^*(r, r_1; \omega) g_f(r + \xi, r_1; \omega) \sigma_\sigma^2(r_1; \omega)$$

where the averaging is done over an infinite number of different outcomes of the scatterer distribution, i.e. ensemble averaging. From Eq.(14) we note that we can use the following approximation a) $$R_{yf}(r, \xi; \omega) = \langle y_f^*(r; \omega) y_f(r + \xi; \omega) \rangle = e^{-ik|r - r_f| + ik|r + \xi - r_f|} \qquad (16)$$

$$e^{ik|r - r_1| - ik|r + \xi - r_1|}$$

$$\approx e^{ik(\varepsilon_1 - \varepsilon_f)\xi}$$

b) $$R_f(r, \xi; \omega) \approx |P(\omega)|^2 \int_{V_f} d^3 r_1 e^{ik(\varepsilon_1 - \varepsilon_f)\xi} \sigma_\sigma^2(r_1; \omega)$$

$$= k^4 \sigma_\nu^2 |P(\omega)|^2 \int_{V_f} d^3 r_1 e^{ik(\varepsilon_1 - \varepsilon_f)\xi} |H_t(r_1, r_f; \omega)|^2$$

Inserting the approximation of $H_t$ close to the focal plane as given in Eq.(8), we get $$R_f(r, \xi; \omega) = \qquad (17)$$

$$k^4 \sigma_\nu^2 |P(\omega)|^2 \left\{ \int_{V_f} d^3 r_1 e^{-ikJ(\varepsilon_1 - \varepsilon_f)\xi} |H_{et}(r_1, r_f; \omega)|^2 |F(r_1 - r_f)|^2 \right\}^*$$

We note that the two-dimensional, lateral part of the integral is the inverse Fourier transform of $|H_{et}|^2$, while the one-dimensional, longitudinal part of the integral gives a constant. As by Eq.(8) $H_{et}$ is the Fourier transform of $s(r_0, r_f; \omega)$, the above integral can be expressed as $$R_f(r, \xi; \omega) = k^4 \sigma_\nu^2 |P(\omega)|^2 A^2 \int_{S_t} d^2 r_a s(r_a - \xi, r_f; \omega) s^*(r_a, r_f; \omega) \qquad (18)$$

where A is a constant. Especially we note that for zero lag we have $$R_f(r, 0; \omega) = |P(\omega)|^2 \int_{V_f} d^3 r_1 |g_f(r, r_1; \omega)|^2 \sigma_\sigma^2(r_1; \omega) \qquad (19)$$

$$= |P(\omega)|^2 \int_{V_f} d^3 r_1 \left( \frac{r_f}{|r - r_1|} \right)^2 \sigma_\sigma^2(r_1; \omega)$$

$$\approx |P(\omega)|^2 \int_{V_f} d^3 r_1 \sigma_\sigma^2(r_1; \omega)$$

$$= k^4 \sigma_\nu^2 |P(\omega)|^2 \int_{V_f} d^3 r_1 |H_t(r_1, r_f; \omega)|^2$$

and utilizing Eq.(18) we get $$R_f(r, 0; \omega) = k^4 \sigma_\nu^2 |P(\omega)|^2 A^2 \int_{S_t} d^2 r_a |s(r_a, r_f; \omega)|^2 \qquad (20)$$

To find the amplitude-phase screen we express it by its amplitude $a_s$ and phase $\theta_s$ as $$s(r, r_f; \omega) = a_s(r, r_f; \omega) e^{i\theta_s(r, r_f; \omega)} \qquad (21)$$

The amplitude of the screen is obtained from Eq.(15) with zero space displacement $\xi$ $$|s(r, r_f; \omega)| = \sqrt{\frac{R_{yf}(r, 0; \omega)}{R_f(r, 0; \omega)}} \qquad (22)$$

We note that $R_{yf}(\underline{r},\underline{0};\omega)$ is the average power of the received element signal. From Eqs.(15, 20) we have that $$\int_{S_1} d^2 r R_{yf}(\underline{r},\underline{0};\omega) = k^4 \sigma_v^2 |P(\omega)|^2 A^2 \left\{ \int_{S_t} d^2 r_a |s(\underline{r}_a,\underline{r}_f;\omega)|^2 \right\}^2 \qquad (23)$$

Solving for the integral of $|s|^2$ and inserting into Eq.(20) we get $$R_f(\underline{r},\underline{0};\omega) = k^2 \sigma_v |P(\omega)| A \sqrt{\int_{S_t} d^2 r R_{yf}(\underline{r},\underline{0};\omega)} \qquad (24)$$

which inserted into Eq.(22) gives $$|s(\underline{r},\underline{r}_f,\underline{0};\omega)| = \sqrt{\frac{R_{yf}(\underline{r},\underline{0};\omega)}{k^2 \sigma_v |P(\omega)| A \sqrt{\int_{S_1} d^2 r R_{yf}(\underline{r},\underline{0};\omega)}}} \qquad (25)$$

We note that for Gaussian variables we have $$R_{yf}(\underline{r},\underline{0};\omega) = \frac{\pi}{2} \langle |y_f(\underline{r};\omega)| \rangle^2 \qquad (26)$$

This gives the following modified estimation of the screen amplitude in Eq.(25)

$$|s(\underline{r},\underline{r}_f;\omega)| = \langle |y_f(\underline{r};\omega)| \rangle \sqrt[4]{\frac{\pi/2}{k^4 \sigma_v^2 |P(\omega)|^2 A^2 \int_{S_t} d^2 r \langle |y_f(\underline{r};\omega)| \rangle^2}} \qquad (27)$$

To find the phase of the screen, we note that $$\nabla s = \left\{ \frac{\nabla a_s}{a_s} + i \nabla \theta_s \right\} s \implies \nabla \theta_s = Im\left\{ \frac{\nabla s}{s} \right\} = Im\left\{ \frac{s^* \nabla s}{|s|^2} \right\} \qquad (28)$$

We utilize the spatial gradient of the auto-correlation function as $$\nabla_\xi R_{yf}(\underline{r},\underline{\xi};\omega) = s^*(\underline{r},\underline{r}_f;\omega) \nabla_\xi s(\underline{r}+\underline{\xi},\underline{r}_f;\omega) R_f(\underline{r},\underline{\xi};\omega)$$
$$+ s^*(\underline{r},\underline{r}_f;\omega) s(\underline{r}+\underline{\xi},\underline{r}_f;\omega) \nabla_\xi R_f(\underline{r},\underline{\xi};\omega) \qquad (29)$$

Noting that $\nabla_\xi s = \nabla_r s$, we get for zero displacement $\underline{\xi}$ $$\nabla_\xi R_{yf}(\underline{r},\underline{0};\omega) = s^*(\underline{r},\underline{r}_f;\omega) \nabla_r s(\underline{r},\underline{r}_f;\omega) R_f(\underline{r},\underline{0};\omega) +$$
$$|s(\underline{r},\underline{r}_f;\omega)|^2 \nabla_\xi R_f(\underline{r},\underline{0};\omega) \qquad (30)$$

which allows us to calculate $$\nabla_r \theta_s(\underline{r},\underline{r}_f;\omega) = Im\left\{ \frac{s^*(\underline{r},\underline{r}_f;\omega) \nabla_r s(\underline{r},\underline{r}_f;\omega)}{|s(\underline{r},\underline{r}_f;\omega)|^2} \right\} \qquad (31)$$
$$= Im\left\{ \frac{\nabla_\xi R_{yf}(\underline{r},\underline{0};\omega)}{R_{yf}(\underline{r},\underline{0};\omega)} \right\} - Im\left\{ \frac{\nabla_\xi R_f(\underline{r},\underline{0};\omega)}{R_f(\underline{r},\underline{0};\omega)} \right\}$$

We express the auto-correlation function by its amplitude and phase as $$R_{yf}(\underline{r},\underline{\xi};\omega) = A_R(\underline{r},\underline{\xi};\omega) e^{i\theta_R(\underline{r},\underline{\xi};\omega)} \; a) \; R_f(\underline{r},\underline{\xi};\omega) =$$
$$A_{Rf}(\underline{r},\underline{\xi};\omega) e^{i\theta_{Rf}(\underline{r},\underline{\xi};\omega)} \; b) \qquad (32)$$

In analogy with Eq.(28) we get $$a)\; \nabla_\xi \theta_R(\underline{r},\underline{\xi};\omega) = Im\left\{ \frac{\nabla_\xi R_{yf}(\underline{r},\underline{\xi};\omega)}{R_{yf}(\underline{r},\underline{\xi};\omega)} \right\} \qquad (33)$$

$$b)\; \nabla_\xi \theta_{Rf}(\underline{r},\underline{\xi};\omega) = Im\left\{ \frac{\nabla_\xi R_f(\underline{r},\underline{\xi};\omega)}{R_f(\underline{r},\underline{\xi};\omega)} \right\}$$

Comparing with Eq. (31) we hence get $$\nabla_r \theta_s(\underline{r},\underline{r}_f;\omega) = \nabla_\xi \theta_R(\underline{r},\underline{0};\omega) - \nabla_\xi \theta_{Rf}(\underline{r},\underline{0};\omega) \qquad (34)$$

Integrating this expression with respect to $\underline{r}$ hence gives the phase of the screen. We note that $R_f(\underline{r},\underline{0};\omega)$ from Eq.(20) is real, so that the imaginary part of the fraction for $\nabla_\xi \theta_{Rf}(\underline{r},\underline{0};\omega)$ is given by the imaginary part of $\nabla_\xi R_f(\underline{r},\underline{0};\omega)$. From Eq.(15) we note that $$\nabla_\xi R_f(\underline{r},\underline{0};\omega) = |P(\omega)|^2 \int_{V_f} d^3 r_1 g_f^*(\underline{r},\underline{r}_1;\omega) \nabla_r g_f(\underline{r},\underline{r}_1;\omega) \sigma_\sigma^2(\underline{r}_1;\omega) \qquad (35)$$

From Eqs.(15, 33) we hence get $$\nabla_\xi \theta_{Rf}(\underline{r},\underline{0};\omega) = Im\left\{ \frac{\nabla_\xi R_f(\underline{r},\underline{0};\omega)}{R_f(\underline{r},\underline{0};\omega)} \right\} \qquad (36)$$

$$= \frac{\int_{V_f} d^3 r_1 Im\{g_f^*(\underline{r},\underline{r}_1;\omega) \nabla_r g_f(\underline{r},\underline{r}_1;\omega)\} \sigma_\sigma^2(\underline{r}_1;\omega)}{\int_{V_f} d^3 r_1 |g_f(\underline{r},\underline{r}_1;\omega)|^2 \sigma_\sigma^2(\underline{r}_1;\omega)}$$

$$= \frac{\int_{V_f} d^3 r_1 \nabla_r \theta_{gf}(\underline{r},\underline{r}_1;\omega) |g_f(\underline{r},\underline{r}_1;\omega)|^2 \sigma_\sigma^2(\underline{r}_1;\omega)}{\int_{V_f} d^3 r_1 |g_f(\underline{r},\underline{r}_1;\omega)|^2 \sigma_\sigma^2(\underline{r}_1;\omega)}$$

$$\approx \frac{\int_{V_f} d^3 r_1 \nabla_r \theta_{gf}(\underline{r},\underline{r}_1;\omega) \sigma_\sigma^2(\underline{r}_1;\omega)}{\int_{V_f} d^3 r_1 \sigma_\sigma^2(\underline{r}_1;\omega)}$$

where $\theta_{gf}$ is the phase of $g_f$ and we have used the relation in Eq.(28) for $g_f$. From Eq.(14) we have approximated $|g_f|^2 = (r_f/|\underline{r}_1-\underline{r}|)^2 \approx 1$ for $\underline{r}_1$ part of $V_f$. From Eq.(14b) we note that $$\nabla_r \theta_{gf}(\underline{r},\underline{r}_1;\omega) \approx k(\underline{e}_{r1-r} - \underline{e}_{rf-r}) \qquad (37)$$

where $\underline{e}_{r1-r} = (\underline{r}_1-\underline{r})/|\underline{r}_1-\underline{r}|$ and $\underline{e}_{rf-r} = (\underline{r}_f-\underline{r})/|\underline{r}_f-\underline{r}|$ are the unit vectors pointing from $\underline{r}$ to $\underline{r}_1$ and $\underline{r}$ to $\underline{r}_f$, respectively. Inserting this expression into Eq.(36) gives $$\nabla_\xi \theta_{Rf}(\underline{r},\underline{0};\omega) \approx k \frac{\int_{V_f} d^3 r_1 (\underline{e}_{r1-r} - \underline{e}_{rf-r}) \sigma_\sigma^2(\underline{r}_1;\omega)}{\int_{V_f} d^3 r_1 \sigma_\sigma^2(\underline{r}_1;\omega)} \qquad (38)$$

$$= k \frac{\int_{S_f} d^2 r_{1\perp} (\underline{e}_{r1-r} - \underline{e}_{rf-r}) |H_{et}(\underline{r}_1,\underline{r}_f;\omega)|^2}{\int_{S_t} d^2 r_{1\perp} |H_{et}(\underline{r}_1,\underline{r}_f;\omega)|^2}$$

where we in the last expression have substituted Eq.(12) with constant $\sigma_v^2$ and carried though the integration of $\underline{r}_1$ along $\underline{r}_{1\parallel}$ defined as 606 in FIG. 6.

The above expression can be written in the short form as $$\nabla_\xi \theta_{Rf}(\underline{r}, \underline{0}; \omega) \approx k(\underline{e}_{rc-r} - \underline{e}_{rf-r}) \qquad (39)$$

$$\underline{e}_{rc-r} = \frac{\int_{V_f} d^3 r_1 \underline{e}_{r1-r} \sigma_\sigma^2(\underline{r}_1; \omega)}{\int_{V_f} d^3 r_1 \sigma_\sigma^2(\underline{r}_1; \omega)}$$

$$= \frac{\int_{S_f} d^2 r_{1\perp} \underline{e}_{r1-r} |H_{et}(\underline{r}_1, \underline{r}_f; \omega)|^2}{\int_{S_f} d^2 r_{1\perp} |H_{et}(\underline{r}_1, \underline{r}_f; \omega)|^2}$$

where $\underline{e}_{rc-r} = (\underline{r}_c - \underline{r})/|\underline{r}_c - \underline{r}|$ is the unit vector pointing from $\underline{r}$ to the center of gravity $\underline{r}_c$ of $\sigma^2(\underline{r}_1; \omega)$ over $V_f$. In the last expressions of Eqs.(38, 39) the integration is done laterally over the focal surface $S_f$. Inserting Eq.(39) into Eq.(34) gives $$\nabla_r \theta_s(\underline{r}, \underline{r}_f; \omega) = \nabla_\xi \theta_R(\underline{r}, \underline{0}; \omega) - k(\underline{e}_{rc-r} - \underline{e}_{rf-r}) \qquad (40)$$

This equation can be integrated as $$\theta_s(\underline{r}, \underline{r}_f; \omega) = \int_0^{x_1} d\rho_1 \nabla_{\xi 1} \theta_R(\underline{\rho}, \underline{0}; \omega) - \qquad (41)$$

$$k(|\underline{r}_c - \underline{r}| - |\underline{r}_f - \underline{r}|) + \text{const}$$

$$= \int_0^{x_2} d\rho_2 \nabla_{\xi 2} \theta_R(\underline{\rho}, \underline{0}; \omega) -$$

$$k(|\underline{r}_c - \underline{r}| - |\underline{r}_f - \underline{r}|) + \text{const}$$

Figure 7A:
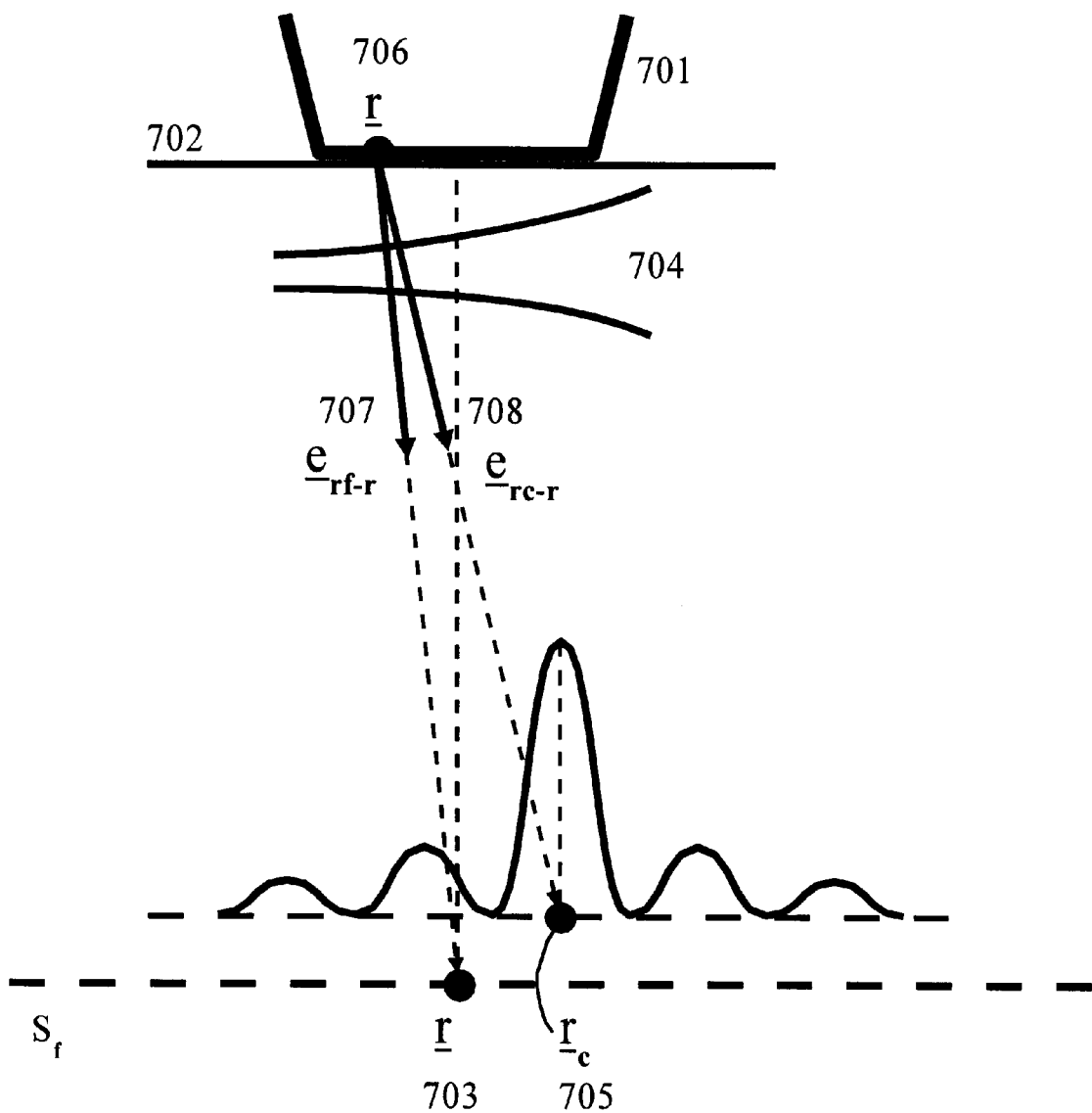
FIG. 7 shows in a) the prism type refraction effect of the ultrasound beam produced by a wedge shaped fat layer in the body wall, and in b) the added effect of miss-estimating the location of the center of gravity of the scatterer distribution by a strong scatterer in the beam side lobe.

We note that the term $-k(|\underline{r}_c - \underline{r}| - |\underline{r}_f - \underline{r}|)$ produces a net refraction and possible change in range of the focus, as illustrated in FIG. 7a where 701 illustrates a transducer array at the skin 702. The focus delays of the transmit beam is set for focusing at $\underline{r}_f$ (703) using the assumption of a homogeneous tissue. A wedge shaped fat layer 704 in the body wall gives a prism like refraction of the focus due to its varying thickness and also modifies the focal distance due to the curvature of the layer surface. These effects move the center of gravity of the transmit beam to $\underline{r}_c$ at 705. The directional unit vectors $\underline{e}_{rf-r}$ and $\underline{e}_{rc-r}$ from a receiver point $\underline{r}$ at 706 on the transducer surface to $\underline{r}_f$ and $\underline{r}_c$ are now found as 707 and 708.

Figure 7B:
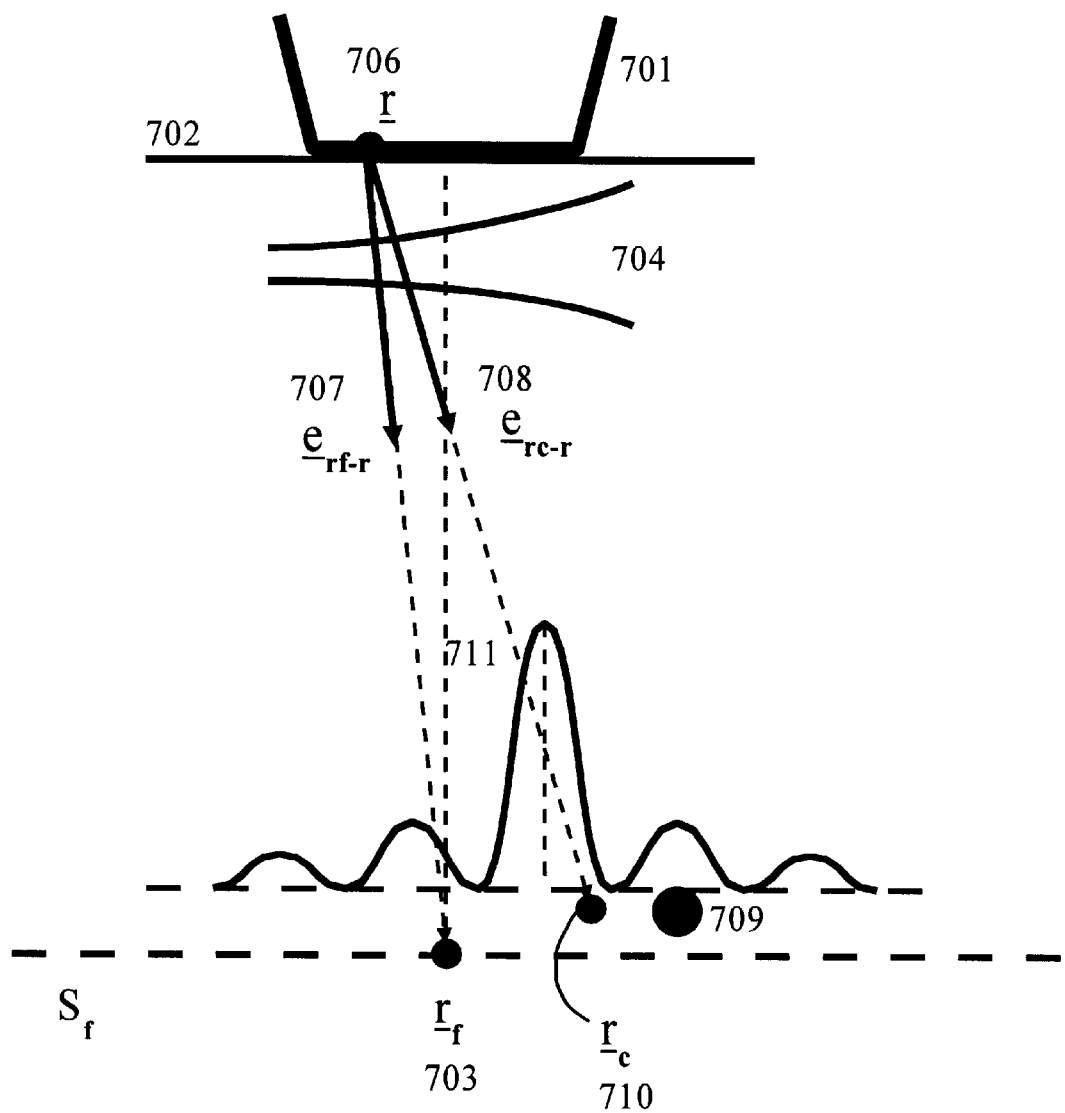

With a homogeneous scatterer distribution the center of gravity of $\sigma^2(\underline{r}_1; \omega)$ over $V_f$ is now found at $\underline{r}_c$. With a heterogeneous scatterer distribution, for example a scatterer distribution that contains a strong scatterer shown as 709 in FIG. 7b at a distance from the predicted beam axis 711, the center of gravity of $\sigma^2(\underline{r}_1; \omega)$ over $V_f$ is further moved to $\underline{r}_c$ at 710.

Hence, deviation of $\underline{r}_c$ from $\underline{r}_f$ can be produced both by a prism like effect of the body wall and by strong scatterers off the beam axis. The last component in $\theta_s$ will therefore produce a direction refraction and modify the focusing of the uncompensated beam, but will not increase the beam width and sidelobes. Such a component hence produces a distortion of the uncompensated image. To further analyze this term, we make the following approximation $$k(\underline{e}_{rc-r} - \underline{e}_{rf-r}) \approx k(\underline{e}_{rc} - \underline{e}_{rf}) \qquad (42)$$

$$= \frac{\int_{S_f} d^2 r_{1\perp}(\underline{e}_{r1} - \underline{e}_{rf}) |H_{et}(\underline{r}_1, \underline{r}_f; \omega)|^2}{\int_{S_f} d^2 r_{1\perp} |H_{et}(\underline{r}_1, \underline{r}_f; \omega)|^2}$$

where $\underline{e}_{rc}$ and $\underline{e}_{rf}$ are the unit vectors pointing from the center of the transducer array onto $\underline{r}_c$ and $\underline{r}_f$, respectively. Inserting Eq.(8) for $H_{et}$, we get $$= \frac{\int_{S_f} d^2 r_{1\perp}(\underline{e}_{r1} - \underline{e})_{rf} \int_{S_t \times S_t} d^2 r_a d^2 r_b e^{ik(\underline{e}_{r1} - \underline{e}_{rf})(\underline{r}_b - \underline{r}_a)} s^*(\underline{r}_a, \underline{r}_f; \omega) s(\underline{r}_b, \underline{r}_f; \omega)}{\int_{S_f} d^2 r_{1\perp} \int_{S_t \times S_t} d^2 r_a d^2 r_b e^{ik(\underline{e}_{r1} - \underline{e}_{rf})(\underline{r}_b - \underline{r}_a)} s^*(\underline{r}_a, \underline{r}_f; \omega) s(\underline{r}_b, \underline{r}_f; \omega)} \qquad (43)$$

We notice that the integration over $\underline{r}_1$ gives $i4\pi^2 \nabla \delta(\underline{r}_a - \underline{r}_b)$ in the numerator and $4\pi^2 \delta(\underline{r}_a - \underline{r}_b)$ in the denominator, which gives $$= \frac{i \int_{S_f} d^2 r_a s^*(\underline{r}_a, \underline{r}_f; \omega) \nabla_{ra} s(\underline{r}_a, \underline{r}_f; \omega)}{\int_{S_f} d^2 r_a |s(\underline{r}_a, \underline{r}_f; \omega)|^2} \qquad (44)$$

Inserting $\nabla s$ from Eq.(28) gives $$= -\frac{\int_{S_t} d^2 r_a \nabla_{ra} \theta_s(\underline{r}_a, \underline{r}_f; \omega) |s(\underline{r}_a, \underline{r}_f; \omega)|^2}{\int_{S_t} d^2 r_a |s(\underline{r}_a, \underline{r}_f; \omega)|^2} + \qquad (45)$$

$$\frac{i \int_{S_t} d^2 r_a \nabla_{ra} |s(\underline{r}_a, \underline{r}_f; \omega)|^2}{2 \int_{S_t} d^2 r_a |a(\underline{r}_a, \underline{r}_f; \omega)|^2}$$

The numerator of the last term can be expanded by Gauss theorem as $$\int_{S_t} d^2 r_a \nabla_{ra} |s(\underline{r}_a, \underline{r}_f; \omega)|^2 = \oint_{\Gamma_t} dr_a \underline{n} |s(\underline{r}_a, \underline{r}_f; \omega)|^2 = 0 \qquad (46)$$

where the last integral is taken along the boundary of $S_t$, and we have assumed that the integration over $S_t$ is enlarged an $\epsilon$-area outside the transducer where the excitation and hence $s$ is zero. Going back to the starting equation, Eq.(42), we now see that $$k(\underline{e}_{rc-r} - \underline{e}_{rf-r}) \approx -\frac{\int_{S_t} d^2 r_a \nabla_{ra} \theta_s(\underline{r}_a, \underline{r}_f; \omega) |s(\underline{r}_a, \underline{r}_f; \omega)|^2}{\int_{S_t} d^2 r_a |s(\underline{r}_a, \underline{r}_f; \omega)|^2} \qquad (47)$$

Inserting Eq.(40) we see that $$\frac{\int_{S_t} d^2 r_a \nabla_\xi \theta_R(\underline{r}, \underline{0}; \omega) |s(\underline{r}_a, \underline{r}_f; \omega)|^2}{\int_{S_t} d^2 r_a |s(\underline{r}_a, \underline{r}_f; \omega)|^2} = 0 \quad (48)$$

We do not in general know $\underline{r}_c$, and the last term in Eqs.(40, 41) is hence unknown. The measurement gives $\nabla_\xi \theta_R$, and to compensate for beam widening and increase in side lobes by the screen, we use an estimate of $\theta_s$ based on the first term in Eqs.(40, 41). As the measurement is subject to noise, we subtract the DC component over $\underline{r}$ of $\nabla_\xi \theta_R$, and use the following estimate for $\nabla_r \theta_s$ $$\nabla_r \hat\theta_s(\underline{r}, \underline{r}_f; \omega) = \nabla_\xi \hat\theta_R(\underline{r}, \underline{0}; \omega) \quad (49)$$

where the hat for $\theta_R$ indicates that any DC-bias has been removed as described. The expression can be integrated to $$\hat\theta_s(\underline{r}, \underline{r}_f; \omega) = \int_0^{x_1} d\rho_1 \nabla_{\xi 1} \hat\theta_R(\underline{\rho}, \underline{\theta}; \omega) \quad (50)$$
$$= \int_0^{x_2} d\rho_2 \nabla_{\xi 2} \hat\theta_R(\underline{\rho}, \underline{0}; \omega)$$

This phase estimate will not correct for refraction and focusing offset due to a plane/spherical component with $\underline{r}_c \neq \underline{r}_f$ in $\theta_s$, and would hence produce the same geometric distortion of the ultrasound image as the uncorrected image, but with improved resolution and less acoustic noise. The effect of strong scatterers off the beam axis can for example be compensated for by the method given in Eq.(59) or by omission of the lower order terms in the Fourier series as discussed in relation to Eq.(95). However, the beam refraction due to prism like effects of the body wall can only be compensated for if we have a point scatterer in $\underline{r}_f$. This beam refraction is analogous to a prism/lens in an optical system. It is not possible to remove this displacement without using point sources at known locations or apriori knowledge of the refracting properties of the prism/lens.

Any DC-offset of $\nabla \theta_R$ could also be removed after the integration in Eq.(41) by subtracting a plane component from the integral, i.e. we first estimate an unmodified $\theta_s$ for example as $$\theta_s(\underline{r}, \underline{r}_f; \omega) = \int_0^{x_1} d\rho_1 \nabla_{\xi 1} \theta_R(\underline{\rho}, \underline{0}; \omega) \quad (51)$$
$$= \int_0^{x_2} d\rho_2 \nabla_{\xi 2} \theta_R(\underline{\rho}, \underline{0}; \omega)$$

and then modify the estimate by subtracting a plane component as $$\hat\theta_s(\underline{r}, \underline{r}_f; \omega) = \theta_s(\underline{r}, \underline{r}_f; \omega) - k_1 x_1 - k_2 x_2 \quad (52)$$

where $k_1$ and $k_2$ for example can be determined by minimizing the following functional $$J(k_1, k_2) = \int_{S_t} d^2 r |s(\underline{r}, \underline{r}_f; \omega)|^2 (\theta_s(\underline{r}, \underline{r}_f; \omega) - k_1 x_1 - k_2 x_2)^2 \quad (53)$$

which gives $$k_1 = \frac{A_{22} B_1 - A_{12} B_2}{A_{11} A_{22} - A_{12}^2} \quad A_{ij} = \int_{S_t} d^2 r x_i x_j |s(\underline{r}, \underline{r}_f; \omega)|^2 \quad (54)$$
$$k_2 = \frac{A_{11} B_2 - A_{12} B_1}{A_{11} A_{22} - A_{12}^2} \quad B_i = \int_{S_t} d^2 r x_i |s(\underline{r}, \underline{r}_f; \omega)|^2 \theta_s(\underline{r}, \underline{r}_f; \omega)$$

This method would also be useful where $\theta_s$ has been estimated with other methods than that described above, for example using the maximum likelihood method or the reference signal method described below.

The uncorrected transmit beam will have increased width of the mainlobe and high sidelobes. The approximation in Eq.(14a) that $s(\underline{r},\underline{r}_1;\omega) \approx s(\underline{r},\underline{r}_f; \omega)$ can hence be less good, which will produce phase estimates of s that is an average over $\underline{r}_1$. The use of the $2^{nd}$ harmonic component of the transmit pulse for the imaging, will give a transmit beam that is less sensitive to phase aberrations, as described in the introduction. However, further improvements of the $2^{nd}$ harmonic transmit beam can be obtained by correcting for phase aberrations and pulse reverberations in the transmit beamformer. Corrections in the receiver beamformer for $2^{nd}$ harmonic imaging, give similar improvements of the receiver beam as with first harmonic imaging.

One hence can use an iterative scheme where a first estimate of the phase-amplitude screen, $s(\underline{r},\underline{r}_f;\omega)$, is obtained with an uncorrected transmit beam, and this first estimate of $s(\underline{r},\underline{r}_f;\omega)$ is used for correction of a second transmit pulse according to Eq.(3) which gives a second set of received element signals that is used for a second estimate of $s(\underline{r},\underline{r}_f; \omega)$, and so on. This iterative estimation will then reduce the aberrations in the transmit beam, and hence improve the approximation in Eq.(14a) that $s(\underline{r},\underline{r}_1;\omega) \approx s(\underline{r},\underline{r}_f;\omega)$. As the transmit beam gets narrower, the effect of strong off axis scatterers are reduced. However, if the effect of such strong scatterers are not removed in the first estimate, for example using the methods in Eq.(59) and discussed in relation to Eq.(95), they will refract the corrected transmit beam and hence produce a refraction in the end estimate.

As stated in relation to Eq.(4), the ensemble averaging above presents practical problems with measurements, where we for a defined image of the tissue are observing a single outcome of the scattering distribution. A first approximation is to substitute ensemble averaging of signal parameters with spatial averaging over several depths along a fixed beam direction, with possible additional averaging of the signal parameters over neighboring beam directions.

There are two problems with this averaging method:
i) Reverberations between structures inside the body wall, and between these structures and the transducer, will produce additive reverberation noise $n_r(\underline{r};\omega)$ to the measurement $y_f(\underline{r};\omega)$, i.e.

$$z_f(\underline{r};\omega) = y_f(\underline{r};\omega) + n_f(\underline{r};\omega) \quad (55)$$

This noise will corroborate the estimates of the correlation functions for $y_f$, and must hence be removed or substantially suppressed before the correlation estimation can bring useful results.*
ii) Variations of the phase aberrations and reverberations with scatterer position limits the size of the averaging region which leaves fundamental variance noise in the estimates of the correlation functions.*

For the problem i) we note that $2^{nd}$ harmonic imaging reduces the acoustic noise from body-wall reverberations, albeit a fair amount of remnant acoustic noise exists. Using the signal from moving or time varying scatterers, further reduction of the acoustic noise can according to the patent be obtained by high-pass filtering of the received element signals from moving or time varying scatterers along the time coordinate of multiple transmit pulses with the same focusing and amplitude. The acoustic noise from reverberations between structures in the body wall, and between the transducer and such structures, are so stationary in time that this high-pass filtering gives strong attenuation of this noise, both for the $1^{st}$ and $2^{nd}$ harmonic image. Typical moving scatterers that can be used, are a moving artery wall, the moving myocardium, the moving blood or other body fluids, and ultrasound contrast agent contained in these materials. Time variable scatterers that are not necessarily moving, can be obtained by using so high incident pulses on contrast agent bubbles in the tissue, producing destruction of at least some of the contrast agent bubbles within the beam, that combined with the inflow of new contrast agent bubbles in the blood perfusion of the tissue, gives a contrast agent scattering distribution that changes between transmit pulses.

Let $\{z_{fk}(\underline{r};\omega), k=1, \ldots, K\}$ be the received signal sequence from a sequence of transmitted pulses, where the subscript k denotes the transmit pulse number. An estimate of the body wall reverberation noise can then be obtained as $$\hat{n}_f(\underline{r};\omega) = \frac{1}{K}\sum_{k=1}^{K} z_{fk}(\underline{r};\omega) \qquad (56)$$

which gives an estimate of the received signal as $$\hat{y}_{fk}(\underline{r};\omega) = z_{fk}(\underline{r};\omega) - \hat{n}_f(\underline{r};\omega) \qquad (57)$$

Such filtering will also remove the signal from stationary scatterers within $V_f$, so that we are left with the signal from the scatterers that are exchanged between transmit pulses, to be used in the ensemble averaging for example in Eqs.(4, 12, 15, 26, 27). An alternative estimate is to filter $z_{fk}$ as a function of k with a non-causal high-pass filter, which gives $$\hat{y}_{fk}(\underline{r};\omega) = H_{HP,k}(z_{fk}(\underline{r};\omega)) \qquad (58)$$

$V_f$ is bounded by the transmit beam, and is hence not strictly bounded in space due to the sidelobes of the transmit beam. Hence, strong and moving scatterers in the sidelobes of the transmit beam can provide interfering signals. These signals have larger angle of inclination to the transducer than the signals within the main lobe, and can hence be attenuated by lowpass filtering $y_{fk}(\underline{r};\omega)$ along the $\underline{r}$-coordinate, so that the final filtering of the received signal before correlation analysis is $$\hat{y}_{fk}(\underline{r};\omega) \approx H_{LP,\underline{r}}\{H_{HP,k}(z_{fk}(\underline{r};\omega))\} \qquad (59)$$

The bandwidth of this lowpass filter is the same as the bandwidth of $y_f(\underline{r};\omega)$ in the $\underline{r}$-coordinates.

For problem ii) the present patent presents a method to reduce the estimate variances by utilizing the signal from moving or time varying scatterers. The basis for this is that the body wall aberrations and reverberations are comparably stationary in time, so that one can use many transmit pulses for the estimates of the correction filters. With sufficient time lag between consecutive transmit pulses, convection or time variation of the scatterers changes the scatterers in the actual region between transmit pulses. Additional averaging in the statistical analysis can then be done over the received element signals from many transmit pulses with different scatterers. This allows one too choose a spatial range of the signal used in the estimation that is small, minimizing the variation of $s(\underline{r},\underline{r}_1;\omega)$ with scatterer position $\underline{r}_1$ so that the approximation $s(\underline{r},\underline{r}_1;\omega) \approx s(\underline{r},\underline{r}_f;\omega)$ is best possible.

With signal processing in the temporal domain, as described below, one can even use signal ranges down to a fixed, single depth sample for the calculation of the statistical parameters of the element signals. This only requires that the phase aberrations and reverberations are practically independent of scatterer position over the range cell, which is determined laterally by the width of the transmitted beam, and radially by the length of the transmitted pulse. This method hence sets the minimal requirement for invariance of the phase aberrations and reverberations with scatterer position.

As the correlation estimates must be done by averaging over a limited spatial region and a limited number K of transmit pulse measurements, we will have errors in the correlation estimates. These errors will have a correlation length in the displacement coordinate $\underline{\xi}$, and obtaining the phase by integration of the gradient of the phase of the screen as above, will produce cumulative errors in the phase estimate.

Figure 8:
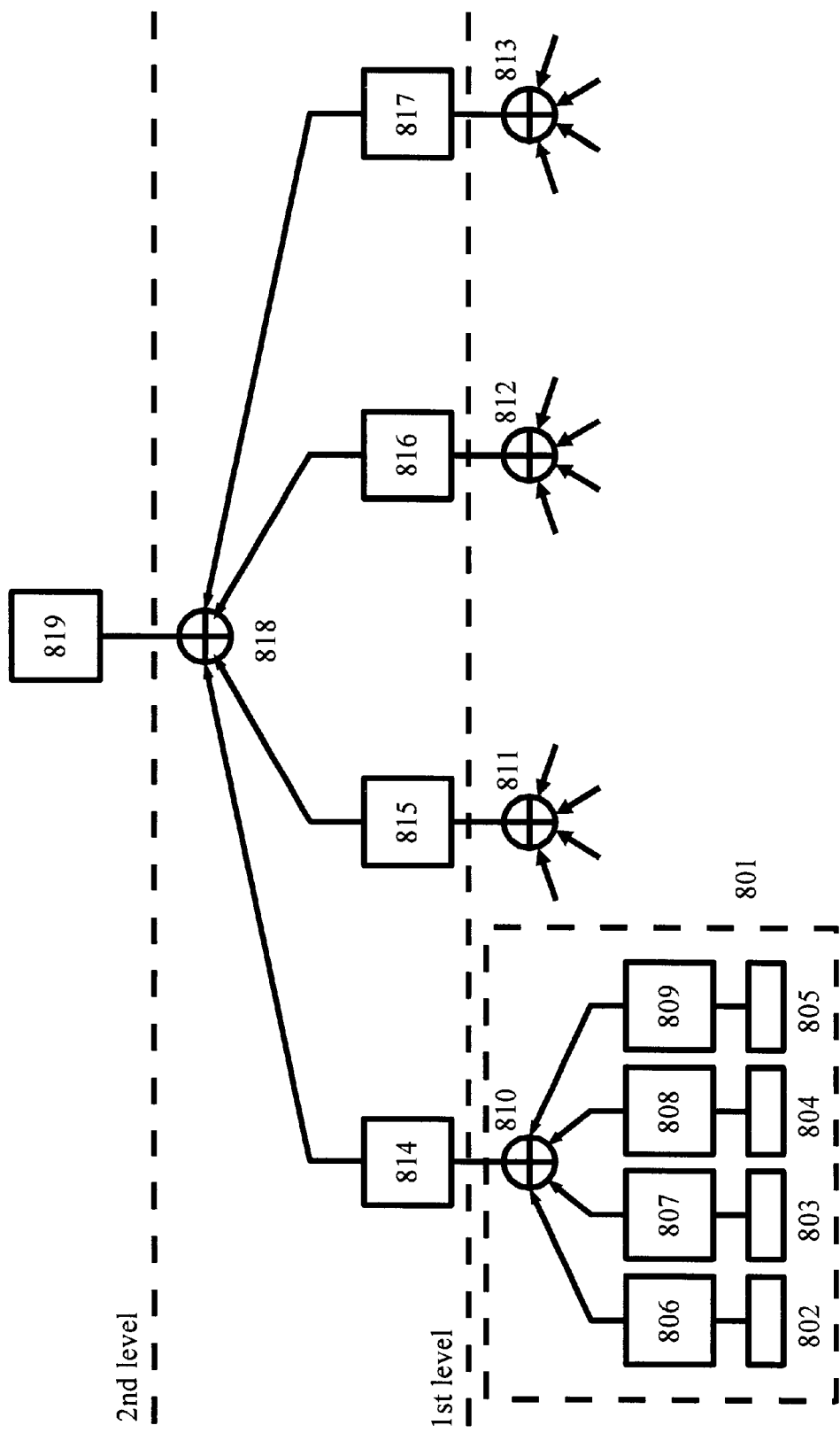
FIG. 8 shows a method of hierarchical integration of the neighbor difference in the phase or delay correlations, to reduce the effect of drift in the integration process produced by estimation errors.

FIG. 8 shows a block diagram of a hierarchical method to integrate the $\nabla \theta_R$, which reduces the cumulative errors compared to using Eq.(50). The amplitude of the screen, is first estimated according to Eqs.(25, 27), and the amplitude of all array element signals are multiplied with $a_s(\underline{r};\omega)$ for amplitude correction according to Eq.(3). The phase gradient is then estimated according to Eq.(40, 49) and integrated for subgroups of neighboring element signals, where the Figure shows in detail one such subgroup 801 which takes in four element signals 802–805 where the estimated phase gradient is integrated and used for phase correction of the element signals in blocks 806–809 and summed in block 810, that is part of a first level of correction for a set of subgroups of all element signals. The Figure shows the summation blocks 811–813 for three additional subgroups at the first level, where for each higher level subgroup the phase gradient between the new element signals is estimated and integrated within each new subgroup, the new element signals being further corrected in blocks 814–817 and summed in block 818, that is part of a second level of correction of second level subgroups of the element signals. This sum together with corrected sums from other subgroups of the $2^{nd}$ level is then grouped into new, $3^{rd}$ level subgroups where the phase gradient estimation and integration together with element signal correction and summation are done as done in the $1^{st}$ and $2^{nd}$ level subgroups, allowing a correction for this sum in the unit 819. This level grouping is then repeated until all element signals are combined into a single, corrected beam signal.

As the phase gradient is integrated only over a limited number of neighboring elements, the integration drift is kept at a minimum.

Other methods to estimate the phase screen are also useful, and we shall here present a method using the maximum likelihood in the Fourier domain, and a method using a reference signal for the correlation For the maximum likelihood method we let m and n label the element signals used for the correction estimation. We assume that possible combination of signals from neighboring elements which are small compared to the correlation length of the body wall disturbances across the array, can be done prior to the estimation, so that the element signals used for the estimation can be different from the array element signals. k labels the signal segments used for averaging, which can be selected as depth ranges for each transmit pulse over several transmit pulses for the same beam direction. Addition of signals from several neighboring beam directions can also possibly be done. We then define a measurement vectors $$\underline{y}_k = \{y_{kn}\} = \{y_{fk}(\underline{r}_n;\omega)\} = \{s(\underline{r}_n,\underline{r}_f;\omega)f_k(\underline{r}_n,\underline{r}_f;\omega)\} = \underline{f}_k S \quad k=1, \ldots, K$$

where we in the vector and matrix notations have omitted $\omega$ for simplicity, defining $$\underline{f}_k = \{f_{kn}\} = \{f_k(\underline{r}_n,\underline{r}_f;\omega)\} \quad S = \{S_{mn}\} = \{s(\underline{r}_n,\underline{r}_f;\omega)\delta_{mn}\} \quad (60)$$

We also use the compact notation $$\underline{y}_K = \{\underline{y}_k, k=1, \ldots, K\}$$

The conditional probability of obtaining the measurement $\underline{y}_K$, given the phase screen matrix S, is then $$p(\underline{y}_K | S) = \prod_k p(\underline{y}_k | S) = \left(\frac{1}{\pi^N |Y|}\right)^k \exp\left\{-\sum_k \underline{y}_k Y^{-1} \underline{y}_k^*\right\} \quad (61)$$

$$= \frac{1}{\pi^{NK} |S|^{2K} |F|^K} \exp\left\{-\sum_k \underline{y}_k S^{-1} F^{-1} (S^*)^{-1} \underline{y}_k^*\right\}$$

$$= \frac{1}{\pi^{NK} |S|^{2K} |F|^K} \exp\left\{-\sum_k (\underline{y}_k S^{-1}) F^{-1} (\underline{y}_k S^{-1})^*\right\}$$

where we have defined $$<\underline{y}_k^* \underline{y}_l> = Y\delta_{kl} \quad Y = \{Y_{mn}\} = \{<y^*_{km} y_{kn}>\} = S^* <\underline{f}^*_k \underline{f}_k> S = S^* F S$$

$$<\underline{f}^*_k \underline{f}_l> = F\delta_{kl} \quad F = \{F_{mn}\} = \{<f^*_{km} f_{kn}>\}$$

We now determine the S that maximizes the $p(\underline{y}_k|S)$. This is equivalent to maximizing the likelihood function $$L(S|\underline{y}_K) = -\ln \pi^{NK} p(\underline{y}_K | S) \quad (62)$$

$$= \sum_k (\underline{y}_k S^{-1}) F^{-1} (\underline{y}_k S^{-1})^* + 2K \ln|S| + K \ln|F|$$

$$= \sum_{k,m,n} (F^{-1})_{mn} \frac{y_{km} y^*_{kn}}{s_m s_n} + 2K \ln \prod_m |s_m| + K \ln|F|$$

with respect to $a_{sn}$ and $\theta_{sn}$. We now assume that $a_{sn}$ is determined from the formula in Eqs.(25, 27), and we set out to maximize L with respect to $\theta_{sn}$. We then write $$L(S|\underline{y}_k) = \sum_{m,n} (F^{-1})_{mn} e^{i(\theta_{sn} - \theta_{sm})} \sum_k \tilde{y}_{km} \tilde{y}^*_{kn} + \quad (63)$$

$$2K \ln \prod_m a_{sm} + K \ln|F|$$

$$\tilde{y}_{km} = y_{km} / a_{sm}$$

Differentiating L with respect to $\theta_{sp}$ gives $$\frac{\partial L}{\partial \theta_{sp}} = ie^{i\theta_{sp}} \sum_m (F^{-1})_{mp} e^{-i\theta_{sm}} R_{mp} - \quad (64)$$

$$ie^{-i\theta_{sp}} \sum_n (F^{-1})_{pn} e^{i\theta_{sn}} R_{pn}$$

$$= 0$$

-continued $$R_{mn} = \sum_k \tilde{y}_{km} \tilde{y}^*_{kn}$$

where $R_{mn}$ is the correlation function estimate of the element signals at array points m and n, estimated for the K averaging elements. Eq.(64) can be written in compact form as $$\frac{\partial L}{\partial \theta_{sp}} = 2Im\left\{e^{-i\theta_{sp}} \sum_n (F^{-1})_{pn} e^{i\theta_{sn}} R_{pn}\right\} = 0 \quad (65)$$

The expression in the brackets hence must be real, which requires that $$\theta_{sp} = \text{Phase}\left\{\sum_n (F^{-1})_{pn} e^{i\theta_{sn}} R_{pn}\right\} \quad (66)$$

This is a non-linear equation, which can be solved with several numerical iteration schemes, for example as $$\theta_{sp,q+1} = \theta_{sp,q} + \mu\left(\text{Phase}\left\{\sum_n (F^{-1})_{pn} e^{i\theta_{sn,r}} R_{pn}\right\} - \theta_{sp,q}\right) \quad (67)$$

where q labels the iteration step. A starting value for the iteration can be $\theta_{sp,0}=0$, or we can use the result of integration of the nearest neighbor correlation from Eq.(50). The parameter $\mu$ is then selected for adequate convergence of the iteration scheme.

A reference signal can for example be obtained as the full sum of all the receive element signals, referred to as the beam sum reference, or as a sum of subgroups of the receive element signals, referred to as a subgroup reference. The subgroup reference is for example useful with hierarchical methods as described in FIG. 8, where each subgroup can use a subgroup reference formed as the sum of the signals in the subgroup.

An advantage with the use of the reference signal is that the screen amplitude and phase can for each receiver channel be determined by correlation between the element signal for this channel and the reference signal, hence avoiding the integration in Eq.(50) with its drift problems.

A reference signal of the type described, can then be expressed as $$r_{fk}(\omega) = \int_{S_t} d^2 r_a w(\underline{r}_a;\omega) y_{fk}(\underline{r}_a;\omega) \quad (68)$$

$$= P(\omega) \int_{S_t} d^2 r_a w(\underline{r}_a;\omega) s(\underline{r}_a, \underline{r}_f;\omega)$$

$$\int_{V_f} d^3 r_1 g_f(\underline{r}_a, \underline{r}_1;\omega) \sigma_k(\underline{r}_1;\omega)$$

$$w(\underline{r};\omega) = \begin{cases} \text{apodization weight} & \text{for } \underline{r} \in S_w \\ 0 & \text{else} \end{cases}$$

where the label k indicates transmit pulse number and $S_w$ defines the subgroup of elements that contributes to the reference signal, which can be a single element signal, a subgroup of element signals, or all element signals which gives the beam sum. $w(\underline{r};\omega)$ is allowed to have a frequency variation which means that it can implement aberration corrections. With iterative estimation of s, as described above, one can use $w(\underline{r};\omega)=s_q^*(\underline{r},\underline{r}_f;\omega)$, where q denotes the estimate of s at iteration step no. q, to correct for the aberrations in the reference signal. As a function of $\underline{r}$ it is a weighting function which can be set to unity for equal weight, or can be used as an apodization function over the subgroup.

The correlation between the reference signal and an element signal is then $$\langle r_f^*(\omega) y_f(\underline{r};\omega) \rangle = s(\underline{r}, \underline{r}_f; \omega) |P(\omega)|^2 \int_{S_t} d^2 r_a w(\underline{r}_a; \omega) s^*(\underline{r}_a, \underline{r}_f; \omega) \times \qquad (69)$$

$$\int_{V_f \times V_f} d^3 r_1 d^3 r_2 g_f^*(\underline{r}_a, \underline{r}_1; \omega) g_f(\underline{r}, \underline{r}_2; \omega) \langle \sigma^*(\underline{r}_1; \omega) \sigma(\underline{r}_2; \omega) \rangle$$

where the label k is omitted since we are calculating ensemble averages. Inserting the δ-correlation of σ from Eq.(12) then gives $$\langle r_f^*(\omega) y_f(\underline{r};\omega) \rangle = \qquad (70)$$

$$s(\underline{r}, \underline{r}_f; \omega) \int_{S_t} d^2 r_a w(\underline{r}_a; \omega) s^*(\underline{r}_a, \underline{r}_f; \omega) R_f(\underline{r}_a, \underline{r} - \underline{r}_a; \omega)$$

$$R_f(\underline{r}_a, \underline{r} - \underline{r}_a; \omega) = |P(\omega)|^2 \int_{V_f} d^3 r_1 g_f^*(\underline{r}_a, \underline{r}_1; \omega) g_f(\underline{r}, \underline{r}_1; \omega) \sigma_\sigma^2(\underline{r}_1; \omega)$$

Inserting the expression for $R_f$ from Eq.(16b) we get $$\langle r_f^*(\omega) y_f(\underline{r};\omega) \rangle \approx s(\underline{r}, \underline{r}_f; \omega) |P(\omega)|^2 \int_{S_t} d^2 r_a w(\underline{r}_a; \omega) s^*(\underline{r}_a, \underline{r}_f; \omega) \qquad (71)$$

$$\int_{V_f} d^3 r_1 e^{-ik(\underline{e}_1 - \underline{e}_f)(\underline{r}_a - \underline{r})} \sigma_\sigma^2(\underline{r}_1; \omega)$$

$$= s(\underline{r}, \underline{r}_f; \omega) |P(\omega)|^2 \int_{V_f} d^3 r_1 e^{ik(\underline{e}_1 - \underline{e}_f)\underline{r}} \sigma_\sigma^2(\underline{r}_1; \omega)$$

$$\int_{S_t} d^2 r_a e^{-ik(\underline{e}_1 - \underline{e}_f)\underline{r}_a} w(\underline{r}_a; \omega) s^*(\underline{r}_a, \underline{r}_f; \omega)$$

Comparing with Eq.(8) we see that the last integral in Eq.(71) represents the complex conjugate of the focal beam profile of a transducer composed of the elements of $S_w$, which we denote $H_{wt}^*$. This allows us to write $$\langle r_{fk}^*(\omega) y_{fk}(\underline{r};\omega) \rangle = s(\underline{r}, \underline{r}_f; \omega) VZ(\underline{r}) \qquad (72)$$

$$VZ(\underline{r}) = |P(\omega)|^2 \int_{V_f} d^3 r_1 e^{ik(\underline{e}_1 - \underline{e}_f)\underline{r}} H_{wt}^*(\underline{r}_1, \underline{r}_f; \omega) \sigma_\sigma^2(\underline{r}_1; \omega)$$

Inserting Eqs.(12, 9), we get $$VZ(\underline{r}) = k^2 \sigma_v^2 |P(\omega)|^2 \int_{V_f} d^3 r_1 e^{ik(\underline{e}_1 - \underline{e}_f)\underline{r}} |H_{wt}^*(\underline{r}_1, \underline{r}_f; \omega)|^2 |F(r_1 - r_f; \omega)|^2 \qquad (73)$$

$$= k^4 \sigma_v^2 |P(\omega)|^2 A^2 \left\{ \int_{S_f} d^2 r_{1\perp} e^{-ik(\underline{e}_1 - \underline{e}_f)\underline{r}} H_{wt}(\underline{r}_1, \underline{r}_f; \omega) |H_{et}(\underline{r}_1, \underline{r}_f; \omega)|^2 \right\}^*$$

We note that the integral has the form of an inverse Fourier transform in relation to Eq.(8), and further evaluation gives $$VZ(\underline{r}) = k^2 \sigma_v^2 |P(\omega)|^2 B^2 \left\{ \int_{S_t \times S_t} d^2 r_a d^2 r_b s^*(\underline{r}_a - \underline{r}, \underline{r}_f; \omega) s(\underline{r}_a - \underline{r}_b, \underline{r}_f; \omega) w^*(\underline{r}_b; \omega) s(\underline{r}_b, \underline{r}_f; \omega) \right\}^* \qquad (74)$$

$$= k^4 \sigma_v^2 |P(\omega)|^2 B^2 \int_{S_t \times S_t} d^2 r_a d^2 r_b s(\underline{r}_a - \underline{r}, \underline{r}_f; \omega) s^*(\underline{r}_a - \underline{r}_b, \underline{r}_f; \omega) w(\underline{r}_b; \omega) s^*(\underline{r}_b, \underline{r}_f; \omega)$$

We hence see that the phase of the reference signal correlation is the phase of s plus the phase of s convolved three times with itself with intermittent complex conjugation, weighted with $w(\underline{r}_b;\omega)$. This last convolution has in general a phase, so that the phase of the reference signal correlation is different from $\theta_s$.

However, an interesting scheme is to use an iterative procedure where the transmit beam is corrected with each new phase estimate of $\theta_s$. When such a procedure converges, the phase of $VZ(\underline{r})$ will be minimized, and the reference signal correlation will give close to the correct phase estimate of s.

In the above calculations, we have used the Fourier transform of the received signal as a basis for the correlation analysis. The estimation then produces the phase amplitude screen over the complete range of frequencies in the received signal, i.e. both the 1st and the $2^{nd}$ harmonic component of the transmitted frequency band for the tissue signal, and for the contrast agent signal in addition also sub, $3^{rd}$, and $4^{th}$ harmonic bands. Using a correction as in Eq.(3), one will hence in principle correct for the $1^{st}$ harmonic band in the transmit beamformer, while in the receive beamformer Eq.(3) will correct for harmonic components of the transmit band. However, the acoustic noise is lower and the transmit beam is less inflicted by the phase aberrations for the harmonic band of frequencies, compared to the first harmonic band. The estimates of screen amplitude and phase are hence more robust in the harmonic bands.

Since the received signal contains noise, we will in practice only be able to estimate the screen for frequencies where the received signal has adequate power above the noise level. Eqs.(25, 27) for estimation of the screen amplitude is then conveniently modified to limit the estimated amplitude for frequencies with low signal power as $$|s(\underline{r}, \underline{r}_f; \omega)|_W = \langle |y_f(\underline{r};\omega)| \rangle \sqrt[4]{\frac{\pi/2}{R(\omega) + \max_\omega R(\omega)/SN}} \qquad (75)$$

$$R(\omega) = k^4 \sigma_v^2 |P(\omega)|^2 A^2 \int_{S_1} d^2 r \langle |y_f(\underline{r};\omega)| \rangle^2$$

where SN is a signal to noise ratio parameter and the subscript W indicates that the limitation is an approximation to a Wiener-type filter. This formula has a problem that the errors in the estimates produces ringing of the filter impulse response, which propagates through Eq.(3) into the corrected signals. Less ringing is obtained with a Matched filter type of approximation denoted with the subscript M as $$|s(\underline{r}, \underline{r}_f; \omega)|_M = \frac{\langle |y_f(\underline{r}; \omega)| \rangle}{\max_\omega \int_{S_1} d^2 r \langle |y_f(\underline{r}; \omega)| \rangle} \qquad (76)$$

The region in ω where |s| is substantially larger than the noise, then defines frequency bands where estimation of the phase of s can be attempted, and the correction filter amplitude is set softly to zero at the edges of the bands.

One should note that through inverse Fourier transform, the calculations can be done directly on the time varying received element signals according to well known transformations. In this respect, we note from Eq.(14) that the received, steering and focusing compensated signal can be written as $$y_f(\underline{r}; t) = s(\underline{r}, \underline{r}_f; t) \underset{t}{\otimes} f(\underline{r}, \underline{r}_f; t) = \int d\tau s(\underline{r}, \underline{r}_f; \tau) f(\underline{r}, \underline{r}_f; t - \tau) \qquad (77)$$

where $f(\underline{r},\underline{r}_f;t)$ is the signal that would have been received without phase aberrations. The calculations in the time domain become particularly simple when the phase-amplitude screen can be approximated by a pure delay and amplitude distortion as $$s(\underline{r},\underline{r}_f;\omega) = a_s(\underline{r},\underline{r}_f) e^{-i\omega \tau_s(\underline{r},\underline{r}_f)} \qquad (78)$$

The inverse Fourier transform of s is then $$s(\underline{r},\underline{r}_f;t) = a_s(\underline{r},\underline{r}_f) \delta\{t - \tau_s(\underline{r},\underline{r}_f)\} \qquad (79)$$

We note that the impulse response of the compensation filter in Eq.(3) is with this approximation $$h_{tr}(\underline{r},\underline{r}_f;t) = F^{-1}\{H_{tr}(\underline{r},\underline{r}_f;\omega)\} = a_s(\underline{r},\underline{r}_f) \delta\{t + \tau_s(\underline{r},\underline{r}_f)\} \qquad (80)$$

From Eq.(77) we see that we get the following form of the received signal in the temporal domain $$y_f(\underline{r};t) = a_s(\underline{r},\underline{r}_f) f(\underline{r},\underline{r}_f; t - \tau_s(\underline{r},\underline{r}_f)) \qquad (81)$$

The correlation function of the time signal $y_f$ then takes the form $$R_{yf}(\underline{r},\underline{\xi};\tau) = \langle y_f(\underline{r};t) y_f(\underline{r}+\underline{\xi};t+\tau) \rangle = a_s(\underline{r},\underline{r}_f) a_s$$

$$(\underline{r}+\underline{\xi},\underline{r}_f) R_f(\underline{r},\underline{\xi};\tau + \tau_s(\underline{r},\underline{r}_f) - \tau_s(\underline{r}+\underline{\xi},\underline{r}_f))$$

$$R_f(\underline{r},\underline{\xi};\tau) = \langle f(\underline{r},\underline{r}_f;t) f(\underline{r}+\underline{\xi},\underline{r}_f;t+\tau) \rangle \qquad (82)$$

The amplitude can then be estimated from a frequency independent form of Eq.(22) as $$a_s(\underline{r}, \underline{r}_f) = \sqrt{\frac{R_{yf}(\underline{r}, \underline{0}; 0)}{R_f(\underline{r}, \underline{0}; 0)}} \qquad (83)$$

Using the result in Eq.(26) for Gaussian variables, we can use the modified expression $$a_s(\underline{r}, \underline{r}_f) = \frac{\langle |y_f(\underline{r}; t)| \rangle}{\int_{S_1} d^2 r \langle |y_f(\underline{r}; t)| \rangle} \qquad (84)$$

To determine the delay correction $\tau_s$ we can make use of the Hilbert transform of $y_f$ $$y_{fh}(\underline{r};t) = a_s(\underline{r},\underline{r}_f) f_h(\underline{r},\underline{r}_f; t - \tau_s(\underline{r},\underline{r}_f)) \qquad (85)$$

where $f_h$ is the Hilbert transform of f. The cross correlation function between $y_f$ and $y_{fh}$ is $$R_{yh}(\underline{r},\underline{\xi};\tau) = \langle y_f(\underline{r};t) y_{fh}(\underline{r}+\underline{\xi};t+\tau) \rangle =$$

$$a_s(\underline{r},\underline{r}_f) a_s(\underline{r}+\underline{\xi},\underline{r}_f) R_{fh}(\underline{r},\underline{\xi};\tau + \tau_s(\underline{r},\underline{r}_f) - \tau_s(\underline{r}+\underline{\xi},\underline{r}_f))$$

$$R_{fh}(\underline{r},\underline{\xi};\tau) = \langle f(\underline{r},\underline{r}_f;t) f_h(\underline{r}+\underline{\xi},\underline{r}_f hd\ f;t+\tau) \rangle \qquad (86)$$

For small $\underline{\xi}$ we have $R_{fh}(\underline{r},\underline{\xi};0) \approx 0$. Hence, finding the $\tau_0$ that gives $R_{yh}=0$ gives $$\tau_s(\underline{r}+\underline{\xi},\underline{r}_f) - \tau_s(\underline{r},\underline{r}_f) = \tau_0 \qquad (87)$$

The delays can hence be estimated based on the time functions of the element signals through correlation methods that are well developed.

The delay approximations in Eqs.(78–82) are often found only in a limited band of frequencies, which requires that the received element signals are bandpass filtered to exclude noise, and other harmonic bands in the received signal. Especially if one wants to analyze a harmonic band of the received signal, one must bandpass filter the signals for this band to exclude the other harmonic components and noise. We note that this bears resemblance to the Fourier component analysis above, where the Fourier transform actually is a set of bandpass filters for each Fourier frequency component.

By adequate band limiting the received element signals around a center frequency $f_c$, which can be the transmitted center frequency $f_c=f_0$ or the $2^{nd}$ harmonic of the transmitted center frequency $f_c=2f_0$, one can for example calculate $\tau_0$ and hence the spatial gradient of the delay between neighboring element signals as $$\tau_0 \approx \frac{1}{2\pi f_c} \tan^{-1} \frac{R_{yh}(\underline{r}, \underline{\xi}; 0)}{R_{yf}(\underline{r}, \underline{\xi}; 0)} \qquad (88)$$

where $\underline{\xi}$ gives the vector distance between neighboring transducer elements, and $\underline{r}$ gives the position of the transducer elements as above. For such band limited signals the Hilbert transform can be approximated by a delay of the signal of $\frac{1}{4}f_c$, so that we get $$\tau_s(\underline{r}+\underline{\xi}, r_f) - \tau_s(\underline{r}, \underline{r}_f) \approx \frac{1}{2\pi f_c} \tan^{-1} \frac{\langle y_f(\underline{r}+\underline{\xi}; t+1/4f_c) y_f(\underline{r}; t) \rangle}{\langle y_f(\underline{r}+\underline{\xi}; t) y_f(\underline{r}; t) \rangle} \qquad (89)$$

In a correlation process, it is sufficient to filter only one of the signals, as the filter also applies to the other signal in the correlation process. This is specially interesting for correlation with a reference signal as in Eqs.(68–74), as one then can band-pass filter and possibly Hilbert transform only the reference signal, as opposed to also filtering the much larger number of element signals. More specifically we get the reference signal of Eq.(68) in the temporal domain as $$r_f(t) = \int_{S_t} d^2 r_a w(\underline{r}_a) y_f(\underline{r}_a; t) \qquad (90)$$

$$= \int_{S_t} d^2 r_a d\tau w(\underline{r}_a) s(\underline{r}_a, \underline{r}_f; \tau) f(\underline{r}_a, \underline{r}_f; t - \tau)$$

where we for simplicity have neglected possible ω dependence of w in Eq.(68). Such ω variation of w could be included in this analysis also by an added convolution in time of the above expression. With the insertion of Eq.(79) we get with pure amplitude-delay screen $$r_f(t) = \int_{S_t} d^2 r_a d\tau w(r_a) a_s(r_a, r_f) f(r_a, r_f; t - \tau_s(r_a, r_f)) \quad (91)$$

Hilbert transforming and band-pass filtering this signal, for example to select a harmonic band, allows one to calculate the following correlation function $$R_{mrhy}(r; \tau) = \langle r_{mfh}(t) y_f(r; t + \tau) \rangle \quad (92)$$

$$= a_s(r, r_f) \int_{S_t} d^2 r_a d\tau w(r_a) a_s(r_a, r_f)$$

$$R_{mfh}(r_a, r - r_a; \tau + \tau_s(r_a, r_f) - \tau_s(r, r_f))$$

where the subscripts mrh and mfh indicate bandpass filtering around the mth harmonic band and Hilbert transform, i.e.

$$R_{mfh}(r_a, r-r_a; \tau) = \langle f(r_a, r_f; t) f_{mh}(r, r_f; t+\tau) \rangle \quad (93)$$

where the subscript mh indicates bandpass filtering around the mth harmonic band and Hilbert transform.

In many practical situations one find that $$R_{mrhy}(r; \tau_0) = 0 \Rightarrow \tau_0 \approx \tau_s(r, r_f) \quad (94)$$

This is specially true with iterated estimation schemes where the subgroup weighting function is extended to a filter $w(r) \sim w_q(r, \tau)$ which applies the estimated corrections according to Eq.(80) for each step q.

The method of reference signal correlation hence leaves itself for simple processing both for harmonic filtering of any order, Hilbert transforms, etc., as this filtering can be done on the reference signal only, and not necessarily on all the element signals. This could also be formulated that the element signals contains unfiltered components that are uncorrelated to the filtered signals, these components hence being attenuated in the correlation process. Hence, reducing the sensitivity to stationary reverberations could be done only on the reference signal by harmonic band pass filtering or high pass filtering along the transmitted pulse number coordinate. However, in a practical correlation processes with averaging over limited number of samples, one will have rests of these signal components as variance in the final estimate depending on the total number of samples available for averaging. The variance can hence be reduced by filtering both signals before the correlation process.

We also note that the formation of the reference signal produces a spatial lowpass filtering of the element signals along the array element coordinate, which reduces the effect of strong off-axis scatterers according to Eq.(59).

To reduce the estimation variance in the averaging, it is still convenient to use additional averaging over the received signals from moving or time varying scatterers for many consecutive transmit pulses, so spaced apart in time that the scatterers are exchanged for each transmit pulse.

The estimation of the amplitude corrections are based on simple expressions as in Eqs.(22, 25, 27, 75, 83, 84). The largest amount of processing goes into estimation of the phase of s, or the approximate delays of s, and these estimates are also subject to the largest estimation error. The spatial correlation length of the phase of s across the transducer surface, has in most situations a lower limit, which can be used to improve the variance and robustness of the estimates of both $a_s$ and $\theta_s$. For $a_s$ the limited correlation length along the transducer surface allows a spatial lowpass filtering of the estimate of as across the transducer surface, to reduce estimation noise.

For the screen phase $\theta_s$ we can use the limited correlation length to give an apriori specification of $\theta_s$, for example through a truncated generalized Fourier series $$\theta_s(r, r_f; \omega) = \sum_{i,j \in S_{IJ}} \theta_{ij}(r_f; \omega) P_i(x) P_j(y) \quad (95)$$

where the coordinate on the receiver array is given as $r = x \underline{e}_x + y \underline{e}_y$, and $P_i(\cdot)$ are generalized Fourier base functions, for example complex harmonic functions or Legendre polynomials, and the summation set $S_{IJ}$ is typically i=0, 1, ..., I, and j=0, 1, ..., J. For a finite number of transducer elements labeled in the x-direction as m=0, 1, ..., M and in the y-direction as n=0, 1, ..., N, we can get a full representation of the sampled phase function with I=M and J=N, for example as with the Discrete Fourier Transform for complex harmonic base functions. However, enforcing expected correlation properties of $\theta_s$, one can use far fewer base functions, letting $S_{IJ}$ be a subgroup of (0, 1, ..., M)×(0, 1, ..., M). Per the discussion in relation to Eq.(41) and FIG. 7, it is for example natural with Legendre polynomials as base functions to exclude $P_0$ and $P_1$, as they represent a plane tilting of the phase which we want to avoid. One can also give an upper limit of I and J so that Eq.(95) satisfies the expected spatial correlation properties of $\theta_s$.

By renumbering the base functions, we can write Eq.(95) as $$\theta_s(r, r_f; \omega) = \sum_{j \in D_\theta} \theta_j(r_f; \omega) P_j(x, y) = \underline{\theta}(r_f; \omega)^T \underline{P}(x, y) \quad (96)$$

$$\underline{\theta}(r_f; \omega) = \{\theta_j(r_f; \omega), j \in D_\theta\}$$

$$\underline{P}(x, y) = \{P_j(x, y), j \in D_\theta\}$$

where $D_\theta$ defines the subspace that adequately represents the expected spatial correlation properties of $\theta_s$.

One can then for example use the maximum likelihood method as in Eqs.(60–67) to estimate the coefficient vector $\underline{\theta}$. We then note that the phase $\theta_{sn} = \theta_s(r_n, r_f; \omega)$ at location $r_n$ can be expressed as $$\theta_{sn} = \sum_{j \in D_\theta} P_{nj} \theta_j(r_f; \omega) \quad (97)$$

$$P_{nj} = P_j(r_n)$$

Inserting this form of $\theta_s$ into the likelihood function of Eq.(63), we get a modified likelihood function as $$L(\underline{\theta} \mid \underline{y}_K) = \sum_{m,n} (F^{-1})_{mn} e^{i \sum_j (P_{nj} - P_{mj}) \theta_j} R_{mn} + \quad (98)$$

$$2K \ln \prod_m a_{sm} + K \ln |F|$$

$$R_{mn} = \sum_k \frac{y_{km} y_{kn}^*}{a_{sm} a_{sn}}$$

which is maximized when $$\frac{\partial L}{\partial \theta_p} = i \sum_{m,n} (F^{-1})_{mn} (P_{np} - P_{mp}) e^{i \sum_j (P_{nj} - P_{mj}) \theta_j} R_{mn} = 0 \quad (99)$$

$$p \in D_\theta$$

which is a non-linear equation in $\theta_j$ that for example can be solved through iterations.

With an approximation of the screen as in Eq.(79), it is then natural to approximate the delay function as in Eq.(96), i.e.

$$\tau_s(\underline{r}, \underline{r}_f; \omega) = \sum_{j \in D_\tau} \tau_j(\underline{r}_f; \omega) P_j(x, y) = \underline{\tau}(\underline{r}_f; \omega)^T \underline{P}(x, y) \quad (100)$$

$$\underline{\tau}(\underline{r}_f; \omega) = \{\tau_j(\underline{r}_f; \omega), j \in D_\tau\}$$

where $D_\tau$ defines the subspace that adequately represents the expected spatial correlation properties of $\tau_s$. One then only have to estimate a reduced parameter set $\underline{\tau}$.

A block diagram of a possible implementation of the invention for distributed scatterers with short correlation length in an ultrasound imaging system, could be the same as shown in FIG. 3b for the artificial point scatterer situation.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A method for corrections of phasefront aberrations and pulse reverberations in medical ultrasound imaging, where
    ultrasound beams on transmit and/or receive are formed with an ultrasound transducer array that has a two-dimensional distribution of elements, a maximal linear dimension of the elements being smaller than a spatial correlation length of the phase amplitude seen across the array surface,
    a individual array element signals are filtered in a correction filter before standard beam forming is done, both for the transmit and/or the receive beams,
the correction filters are estimated by
    introducing into a soft tissue image field one or more artificial ultrasound point scatterers,
    receiving backscatterd signal from the point scatterers with the transducer array,
    the point scatterers being spaced apart that the signals from the individual scatterers can clearly be discriminated from each other,
    the signals from the point scatterers having characteristics in amplitude or frequency content, or both, so that they are clearly separable from the tissue signal,
    the signals from the individual point scatterers being used to derive correction filters to correct for phase aberrations and pulse reverberations both in the receive and the transmit beams.

2. A method according to claim 1, where the frequency responses of the element signal correction filters for focusing the transmit and/or the receive beams onto the location of a point scatterer, are obtained by
    Fourier transforming along time coordinate the received element signals from the point scatterers and utilizing the frequency components where amplitude of the Fourier transform is larger than the noise level,
    correcting phase of the Fourier transforms of the element signals by a spherical approximation of a propagation delay from the point scatterer to the array elements, which is in essence a division of the Fourier transform with the Green's function of the Helmholtz equation,
    the complex conjugate of the corrected Fourier transforms of the elements signals being used as transfer functions of element signal correction filters for the receive and/or the transmit beams.

3. A method according to claim 1, where the impulse responses of the element signal correction filters for focusing the transmit and/or the receiver beams onto the location of a point scatterer, are obtained by
    recording the back scattered element signals from the point scatterer and delay correcting these element signals by a spherical approximation of propagation delay from the point scatterer to the individual array elements,
    using time inverted version of the delay corrected element signals as impulse responses for the element signal correction filters for the receive and/or the transmit beams.

4. A method according to claim 2, where the correction filters are approximated by delay and amplitude corrections.

5. A method according to claim 4, where for focusing the beam onto the location of a point scatterer
    the amplitude corrections for each element signal are obtained as the amplitude of the received element point scatterer signals, and
    the time delay corrections are obtained by comparing arrival times on each element signal channel of the pulses from the point scatterer.

6. A method according to claim 1, where a $2^{nd}$ harmonic band of the backscattered element signals are used to reduce the pulse reverberations in the backscattered signal for estimation of the correction filters or approximate amplitude and delay corrections.

7. A method according to claim 1, where the artificially introduced point scatterers are attached to an intervention tool that is inserted into the body.

8. A method according to claim 7, where the point scatterers are made as indentations in a smooth tool surface, or scatterers attached to a smooth tool surface, or scatterers buried in indentations in the smooth tool surface.

9. A method according to claim 1, where the artificially introduced point scatterers are obtained with a dilute concentration of contrast agent bubbles in the blood or other body fluids.

10. A method according to claim 9, where adequate distance between the contrast agent bubbles are obtained by first destroying the contrast agent bubbles in a selected imaging region, and performing the correction estimation in a subsequent time interval where adequate inflow of new contrast agent bubbles to the region has occurred.

11. A method according to claim 9, where steadily new point scatterers with varying locations and adequate distances are obtained by using high amplitude of the transmitted pulses that continuous destruction of some contrast agent bubbles occurs, while new contrast agent bubbles enters the region with the blood or other body fluids.

12. A method according to claim 7 where the point scatterers on the intervention tool are made by contrast agent bubbles.

13. A method according to claim 9, where the signals from the point scatterers are discriminated from the tissue signal by using frequency components in a sub, $2^{nd}$, $3^{rd}$, or $4^{th}$ harmonic band of the fundamental frequency band of the transmitted pulse.

14. A method according to claim 9, where a coded sequence is transmitted at the contrast agent bubbles, and pulse compression is used in the receiver to enhance the signal to noise ratio of the received signal from the contrast agent bubble, to improve the detection of the contrast agent bubble.

15. A method for corrections of phasefront aberrations and pulse reverberations in medical ultrasound imaging, where the ultrasound beams on transmit and/or receive are formed with an ultrasound transducer array that has a two-dimensional distribution of elements, a maximal linear dimension of the elements being smaller than a spatial correlation length of the phase amplitude seen across the array surface, individual array element signals being filtered in correction filters before standard beam forming is done, both for the transmit and/or the receive beams, the correction filters being estimated from the received element signals from the array elements back scattered from a distribution of scatterers with short correlation length, using an estimation algorithm for the correction filters that reduces the effect of pulse reverberations in the back-scattered signal in a final estimate of correction filters.

16. A method according to claim 15, where a $2^{nd}$ harmonic band of the element signals is used to suppress the pulse reverberations in the element signals.

17. A method according to claim 15, where multiple transmit pulses with the same beam direction and focus is used, and the back scattered element signals for the multiple transmit pulses from moving or time varying scatterers are used for improved estimation of the correction filter responses.

18. A method according to claim 17, where the moving scatterers are scatterers in the blood or other body fluids, the myocardium, or a vessel wall.

19. A method according to claim 18, where the scattering is enhanced by contrast agent bubbles in the moving fluids or tissue.

20. A method according to claim 17, where ultrasound contrast agent bubbles are used for time varying scatterers where transmitted pulse amplitudes are high that destruction of at least some bubbles occur, and new bubbles enter the tissue through the blood or other body fluids.

21. A method according to claim 19, where the signal from the contrast agent bubbles is enhanced over that from the tissue signal and pulse reverberations, by using sub, $2^{nd}$, $3^{rd}$, or $4^{th}$ harmonic components of the backscattered signal from the contrast agent bubbles.

22. A method according to claim 21, where the signal from the contrast agent bubbles is further enhanced by transmitting coded pulse sequences and using pulse compression in the receiver to enhance a signal to noise ratio of the received signal from the contrast agent.

23. A method according to claim 17, where the effect of pulse reverberations in the estimate is suppressed by high pass filtering the received element signals along the pulse number coordinate for each depth sample.

24. A method according to claim 17, where temporal averaging of correction filter parameters along a pulse number coordinate is used to reduce a estimation variance of the parameters.

25. A method according to claim 15, where errors introduced in the estimates of the correction filters by strong, off axis scatterers is reduced by lowpass filtering the received element signals along an element position coordinate along the array surface.

26. A method according to claim 15, where the correction filter frequency responses are estimated from the temporal Fourier transform of the received element signals, where the amplitude of the frequency response is estimated as the average of a amplitude of this Fourier transform for each frequency, within bands where the amplitude is larger than the noise power, and slowly set to zero outside these bands.

27. A method according to claim 26, where phases of the correction filters for each frequency are estimated based on correlation methods.

28. A method according to claim 27, where the phases of the correction filters for each frequency are estimated by integration of the phases of the correlation functions between neighboring element signals.

29. A method according to claim 28, where a plane skew in the phases of the correction filters over the array is removed either after integration, or through removing the DC component of the neighbor correlations before the integration.

30. A method according to claim 28, where the integration of the neighbor phase correlation is broken into several hierarchical levels, where in a first level the element signals are grouped in subgroups of limited number of neighboring elements, where the neighbor phase integration is carried through in each subgroup, and the element signals within each subgroup are corrected and summed together to form a new set of element signals on a higher level, where neighbors on the new level are grouped together in subgroups, and the phase estimates between the neighbors on the new level are integrated in the new subgroups, and the element signals in the new subgroups are corrected and summed to form a new, second level of corrected element signals, continuing this leveling process, by grouping, phase gradient estimation and integration, and signal correction and summing for neighboring elements in the same manner for each new level until all original element signals are combined into a single, corrected beam signal, the final original element correction filters being obtained as a product of all participating correction transfer functions on all levels for the path of that particular element signal.

31. A method according to claim 26, where the phases of the correction filters for each frequency are estimated according to a parameter estimation scheme, for example a maximum likelihood scheme.

32. A method according to claim 15, where the correction filters are approximated by delay and amplitude corrections, where the amplitude corrections for an element signal are determined by averaging the element signal amplitudes over depth and over time between transmit pulses for moving or time varying signals.

33. A method according to claim 32, where the delay corrections are estimated by correlation methods.

34. A method according to claim 33, where the delay corrections are estimated by integration of the delays between neighboring element signals obtained through correlation analysis.

35. A method according to claim 34, where a plane skew in the delays of the correction filters over the array is removed either after the integration, or through removing the DC component of the neighbor delays before the integration.

36. A method according to claim 34, where the integration of the neighbor delays is broken into several hierarchical levels, where in a first level the element signals are grouped in subgroups of limited number of neighboring elements, where the neighbor delay integration is carried through in each subgroup, and the element signals within each subgroup are corrected and summed together to form a new set of element signals on a higher level, where neighbors on the new level are grouped together in subgroups, and the delay estimates between the neighbors on the new level are integrated in the new subgroups, and the element signals in the new subgroups are corrected and summed to form a second level of corrected element signals, where the grouping, delay gradient estimation and integration, and signal correction and summing are done for neighboring elements in the same manner for each level until all original element signals are combined into a single, corrected beam signal, the final original delays being obtained as a sum of the delays on all levels for the path of that particular element signal.

37. A method according to claim 33, where the delay corrections are estimated by correlation between element signals and Hilbert transforms of element signals.

38. A method according to claim 32, where the correction delays are estimated through a parameter estimation scheme, for example a maximum likelihood scheme.

39. A method according to claim 15, where the number of element signals used for estimation of the correction filters is reduced by combining the element signals from neighboring, small array elements into groups where a total dimension of the combined array elements in each group being smaller than the correlation length of the phase aberrations and pulse reverberations.

40. A method according to claim 15, where a minimal parameter representation of the phase or delay corrections are represented by a truncated generalized Fourier series over an element position coordinate, the number of elements in the series being chosen so that the correlation properties of the phase or delay corrections are represented, coefficients in the series forming the parameters to be estimated.

41. A method according to claim 15, where the phase or delay corrections are estimated by correlation analysis of the element signals with a reference signal obtained by combinations of element signals or a parts of the element signals.

42. A method according to claim 41, where only the reference signal is filtered in any harmonic bands, Hilbert transformed, or pulse to pulse high-pass filtered to remove the stationary reverberation components, before the correlation analysis.

43. A method according to claim 15, where estimates of the correction filters are used to correct new transmit beams producing new backscattered element signals to be used for new estimations of the correction filters, in an iterative manner.

* * * * *